United States Patent
Kawaminami et al.

(10) Patent No.: US 8,039,248 B2
(45) Date of Patent: Oct. 18, 2011

(54) MODIFIED FLAVIN ADENINE DINUCLEOTIDE DEPENDENT GLUCOSE DEHYDROGENASE

(75) Inventors: Hiroshi Kawaminami, Tsuruga (JP); Yuji Tsuji, Tsuruga (JP); Masao Kitabayashi, Tsuruga (JP); Yoshiaki Nishiya, Tsuruga (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 151 days.

(21) Appl. No.: 12/547,276

(22) Filed: Aug. 25, 2009

(65) Prior Publication Data

US 2009/0317848 A1    Dec. 24, 2009

Related U.S. Application Data

(62) Division of application No. 11/939,348, filed on Nov. 13, 2007, now Pat. No. 7,662,600.

(60) Provisional application No. 60/868,249, filed on Dec. 1, 2006, provisional application No. 60/892,761, filed on Mar. 2, 2007.

(30) Foreign Application Priority Data

| Nov. 14, 2006 | (JP) | 2006-308337 |
|---|---|---|
| Nov. 14, 2006 | (JP) | 2006-336351 |
| Feb. 16, 2007 | (JP) | 2007-035978 |
| Feb. 16, 2007 | (JP) | 2007-035979 |
| Feb. 16, 2007 | (JP) | 2007-035980 |
| Feb. 26, 2007 | (JP) | 2007-045372 |

(51) Int. Cl.
    *C12M 1/34*      (2006.01)
    *C12Q 1/54*      (2006.01)
    *C12Q 1/52*      (2006.01)
    *C12N 9/04*      (2006.01)
    *C12N 9/24*      (2006.01)

(52) U.S. Cl. ....... 435/287.1; 435/14; 435/161; 435/190; 435/200

(58) Field of Classification Search .............. 435/287.1, 435/14, 16, 190, 200
See application file for complete search history.

(56) References Cited

U.S. PATENT DOCUMENTS

| 2003/0232418 A1 | 12/2003 | Takeshima et al. |
|---|---|---|
| 2006/0063217 A1 | 3/2006 | Omura et al. |
| 2008/0248514 A1 * | 10/2008 | Inamori et al. ................. 435/26 |

FOREIGN PATENT DOCUMENTS

| EP | 1 367 120 A2 | 12/2003 |
|---|---|---|
| EP | 1 862 543 A1 | 12/2007 |
| EP | 2 022 850 A1 | 2/2009 |
| JP | 2004-344145 A | 12/2004 |
| WO | WO 2004/058958 A1 | 7/2004 |
| WO | WO 2006/068170 A1 | 6/2006 |
| WO | WO 2006/101239 A1 | 9/2006 |

OTHER PUBLICATIONS

Tsujimura et al., *Biosci. Biotechnol. Biochem.*, 70(3): 654-659 (2006).

Bak et al., *Biochimical et Biophysica Acta*, 139(2): 277-293 (1967).

* cited by examiner

*Primary Examiner* — Ganapathirama Raghu
(74) *Attorney, Agent, or Firm* — Leydig, Voit & Mayer, Ltd.

(57) ABSTRACT

The invention provides a modified flavin adenine dinucleotide dependent glucose dehydrogenase (FADGDH), as well as a glucose sensor comprising the modified FADGDH and a method for measuring glucose comprising using the glucose sensor to measure glucose of a sample.

2 Claims, 1 Drawing Sheet

US 8,039,248 B2

MODIFIED FLAVIN ADENINE DINUCLEOTIDE DEPENDENT GLUCOSE DEHYDROGENASE

CROSS-REFERENCE TO RELATED APPLICATIONS

This patent application is a divisional of U.S. patent application Ser. No. 11/939,348, filed Nov. 13, 2007, now U.S. Pat. No. 7,662,600, which claims the priority of U.S. Provisional Patent Application No. 60/892,761, filed Mar. 2, 2007, and U.S. Provisional Patent Application No. 60/868, 249, filed Dec. 1, 2006.

INCORPORATION-BY-REFERENCE OF MATERIAL ELECTRONICALLY SUBMITTED

Incorporated by reference in its entirety herein is a computer-readable nucleotide/amino acid sequence listing submitted herewith in computer readable form and identified as follows: 33,624 bytes ASCII (Text) file named "705354SequenceListing.txt," created Aug. 24, 2009.

TECHNICAL FIELD

The present invention relates to a modified glucose dehydrogenase (GDH) with improved heat stability, and further relates to a modified flavin adenine dinucleotide dependent glucose dehydrogenase (FADGDH) having flavin adenine dinucleotide (FAD) as a coenzyme, a process for producing the same, and a glucose sensor.

BACKGROUND ART

Self-monitoring of blood glucose is important for people with diabetes to be aware of their usual glucose levels and use them for their treatment. Enzymes having glucose substrates are employed as sensors for blood glucose self-monitoring. Examples of such enzymes include glucose oxidase (EC 1.1.3.4). Glucose oxidase has the advantages of being highly specific to glucose and having high heat stability. For this reason, it has been used as an enzyme in blood glucose sensors. The first announcement of such properties goes back to as long as 40 years ago. In blood glucose sensors that utilize glucose oxidase, the blood glucose level is measured when electrons generated in the process of converting glucose to D-glucono-d-lactone by oxidization are conducted to an electrode via a mediator. However, glucose oxidase poses a problem in that it tends to transfer protons produced by the reaction to oxygen, causing dissolved oxygen to adversely affect the measured values.

To solve such a problem, for example, NAD(P) dependent glucose dehydrogenase (EC 1.1.1.47) or pyrroloquinoline quinone (hereinafter also referred to as "PQQ" in the specification) dependent glucose dehydrogenase (EC1.1.5.2 (former EC1.1.99.17)) is used as an enzyme in blood glucose sensors. They have the advantage of being free from the influence of dissolved oxygen. However, the former, i.e., NAD(P) dependent glucose dehydrogenase (hereinafter also referred to as "NADGDH" in the specification) has poor stability and is cumbersome, requiring the addition of a coenzyme. The latter, i.e., PQQ dependent glucose dehydrogenase (hereinafter also referred to as "PQQGDH" in the specification), has the drawbacks of having poor substrate specificity and reacting to saccharides other than glucose, such as maltose and lactose, thereby deteriorating the accuracy of the measurement values.

Further, Patent Document 1 discloses *Aspergillus*-flavin-bound glucose dehydrogenase (hereinafter also referred to as "FADGDH"). Since the activity of this enzyme on xylose is only 10% of that on glucose, in the case of measuring the blood glucose level of a person who is taking a xylose tolerance test, the accuracy of the measured value may be impaired. The enzyme has a residual activity ratio of about 89% after treatment at 50° C. for 15 minutes, thereby exhibiting good heat stability. Patent Document 2 discloses the gene sequence and amino acid sequence of the enzyme.
Patent Document 1 WO2004/058958
Patent Document 2 WO2006/101239

DISCLOSURE OF THE INVENTION

Problems to be Solved by the Invention

An object of the present invention is to provide a more practically advantageous enzyme that can be used as a reagent for blood glucose measurement in comparison with the above known enzymes used in blood glucose sensors.

Means for Solving the Problems

Patent Document 2 discloses that flavin-bound glucose dehydrogenase was obtained by incubating a wild-type strain of an *Aspergillus terreus* subspecies in liquid culture or in wheat bran culture, and that enzymes obtained by expressing genes coding for *Aspergillus-terreus*-derived flavin-bound glucose dehydrogenase in recombinant *Escherichia coli*, recombinant fungus (*Aspergillus oryzae*), and recombinant yeast (Genus *Candida*), respectively, were purified.

Patent Document 2 further discloses characteristic tests of these enzymes and some examples showing specific property comparisons of these enzymes when used as sensors.

However, the present inventors believed that Patent Document 2 did not fully disclose enough about these enzymes from the viewpoint of industrial applicability and may not even satisfy the industrial applicability requirement. For example, the enzyme expressed in *E. coli* was considered to be most applicable to mass production, one of the important conditions in industrial requirement; however, there is no description of the temperature stability, another very important condition, of such an enzyme. The present inventors then studied the prior art further, considering the mass production of the enzyme by using gene recombination, to stably supply the enzyme. Moreover, the inventors continued their studies, aiming to provide a more practically advantageous enzyme with reduced activity on xylose by suitably modifying the amino acid sequence of *Aspergillus-oryzae*-derived FADGDH and hence usable as a reagent for blood glucose measurement.

As a result, the inventors found that the *E. coli*-expressed recombinant FADGDH (rFADGHD) thought to be most applicable to mass production had unexpectedly much lower heat stability compared with enzymes produced by incubating and purifying wild-type strains.

For example, an FADGDH the inventors obtained from *Aspergillus oryzae* by the method to be described later had an activity of about 77% after treatment for 15 minutes at 50° C. Whereas the *E. coli*-expressed recombinant FADGDH (raFADGDH) had a heat stability of about 13% after treatment for 15 minutes at 50° C. The heat stability of *Aspergillus terreus* recombinant FADGDH (rtFADGDH) was about 28% after treatment for 15 minutes at 50° C.

Among the enzymes whose structures and for which production processes are disclosed in Patent Document 2, those obtained by being expressed in *E. coli* are presumed to have similarly poorer heat stability than that of enzymes obtained by incubating and purifying wild-type strains.

This presumption is based on the thought that enzymes produced by gene recombination do not have polysaccharides attached on the surface, whereby heat stability is reduced.

During the production process of a blood glucose sensor chip, a heat-drying treatment is sometimes performed. In the case of using a recombinant, heat stability had to be improved due to a risk of drastic heat-inactivation.

The inventors then conducted extensive research with the purpose of providing an enzyme having sufficient heat stability even when produced using gene recombination in *E. coli* and hence being more practically advantageous when used as a reagent for blood glucose measurement.

As a result, the inventors succeeded in solving the aforementioned heat stability problem of the known enzymes for blood glucose sensors by suitably modifying the amino acid sequence of *Aspergillus-oryzae*-derived and *Aspergillus-terreus*-derived FADGDH, and providing a more practically advantageous enzyme usable as a reagent for blood glucose measurement.

More specifically, the present invention provides as follows.

Item 1. A modified FADGDH having improved heat stability through modification.

Item 2. A modified FADGDH according to Item 1, the modified FADGDH being derived from a eukaryote.

Item 3. A modified FADGDH according to Item 1, the modified FADGDH being derived from a filamentous fungus.

Item 4. A modified FADGDH according to Item 1, the modified FADGDH being derived from an *Aspergillus* fungus.

Item 5. A modified FADGDH according to any one of Items 1 to 4, the modified FADGDH having more improved heat stability than wild-type flavin adenine dinucleotide dependent glucose dehydrogenase.

Item 6. A modified FADGDH according to any one of Items 1 to 4, the modified FADGDH having a residual activity of 20% or more in a liquid state after heat treatment at 50° C. for 15 minutes.

Item 7. A modified FADGDH according to any one of Items 1 to 4, the modified FADGDH having a residual activity of 35% or more in a liquid state after heat treatment at 50° C. for 15 minutes.

Item 8. A modified FADGDH according to any one of Items 1 to 4, the modified FADGDH having a residual activity of 40% or more in a liquid state after heat treatment at 50° C. for 15 minutes.

Item 9. A modified FADGDH according to any one of Items 1 to 4, the modified FADGDH having a residual activity of 70% or more in a liquid state after heat treatment at 50° C. for 15 minutes.

Item 10. A modified FADGDH according to any one of Items 1 to 4, the modified FADGDH having a residual activity of 80% or more in a liquid state after heat treatment at 50° C. for 15 minutes.

Item 11. A modified FADGDH having an amino acid sequence represented by SEQ ID No. 2 or SEQ ID No. 46, wherein the modified FADGDH having a primary structure of at least one amino acid being substituted, deleted, inserted or added.

Item 12. A modified FADGDH having improved heat stability, the modified FADGDH having an amino acid substitution at at least one position selected from the group consisting of positions 120, 160, 162, 163, 164, 165, 166, 167, 169, 170, 171, 172, 180, 329, 331, 369, 471 and 551 of SEQ ID No. 2 in the sequence table, at (at least one position selected from the group consisting of positions) 116, 159, 161, 164, 166, 167, 175, 325, 327, 365 and 547 of SEQ ID No. 46 in the sequence table, or at an equivalent position to said positions in an amino acid sequence of another species.

Item 13. A modified FADGDH having improved heat stability, the modified FADGDF having at least any one of the amino acid substitutions K120E, G160E, G160I, G160P, G160S, G160Q, S162A, S162C, S162D, S162E, S162F, S162H, S162L, S162P, G163D, G163K, G163L, G163R, S164F, S164T, S164Y, L165A, L165I, L165N, L165P, L165V, A166C, A166I, A166K, A166L, A166M, A166P, A166S, 167A, S167P, S167R, S167V, N169K, N169P, N169Y, N169W, L170C, L170F, S171I, S171K, S171M, S171Q, S171V, V172A, V172C, V172E, V172I, V172M, V172S, V172W, V172Y, A180G, V329Q, A331C, A331D, A331I, A331K, A331L, A331M, Q331V, K369R, K471R, V551A, V551C, V551T, V551Q, V551S, V551Y, (G160E+S167P), (G160I+S167P), (G160S+S167P), (G160Q+S167P), (S162A+S167P), (S162C+S167P), (S162D+S167P), (S162D+S167P), (S162E+S167P), (S162F+S167P), (S162H+S167P), (S162L+S167P), (G163D+S167P), (S164F+S167P), (S164T+S167P), (S164Y+S167P), (L165A+S167P), (L165I+S167P), (L165P+S171K), (L165P+V551C), (L165V+V551C), (A166C+S167P), (A166I+S167P), (A166K+S167P), (A166K+S167P), (A166M+S167P), (A166P+S167P), (A166S+S167P), (S167P+N169K), (S167P+N169P), (S167P+N169Y), (S167P+N169W), (S167P+L170C), (S167P+L170F), (S167P+S171I), (S167P+S171K), (S167P+S171M), (S167P+S171Q), (S167P+S171V), (S167P+V172A), (S167P+V172C), (S167P+V172E), (S167P+V172I), (S167P+V172M), (S167P+V172S), (S167P+V172T), (S167P+V172W), (S167P+V172Y), (S167P+V329Q), (S167P+A331C), (S167P+A331D), (S167P+A331I), (S167P+A331K), (S167P+A331L), (S167P+A331M), (S167P+A331V), (G163K+V551C), and (G163R+V551C) of SEQ ID No. 2 in the sequence table, at least any one of the amino acid substitutions K116D, K116G, K116L, K116F, K116Q, Q159A, Q159K, Q159N, Q159P, Q159V, Q159L, E161C, N164Y, N164V, N164C, T166F, T166Y, T166W, T167L, T167V, T167S, G175K, S325A, S325G, S325K, S325Q, S325R, S325T, S325V, S325Y, S327E, Q365R, V547S, V547C, V547A, and V547Q of SEQ ID No. 46 in the sequence table, or at least one amino acid substitution at an equivalent position to said positions in an amino acid sequence of another species.

Item 14. A modified FADGDH according to any one of Items 1 to 13, the FADGDH having improved pH stability by modification.

Item 15. A modified FADGDH according to any one of Items 1 to 14, the FADGDH having a residual activity of 80% or more after treatment at 25° C. for 16 hours in the pH range from 4.5 to 6.5.

Item 16. A modified FADGDH according to any one of Items 1 to 15, the FADGDH having a residual activity of 90% or more after treatment at 25° C. for 16 hours in the pH range from 4.5 to 6.5.

Item 17. A modified FADGDH having improved pH stability, the modified FADGDH having an amino acid substitution at at least one position selected from the group consisting of positions 163, 167 and 551 of SEQ ID No. 2, or at an equivalent position to said positions in an amino acid sequence of another species.

Item 18. A modified FADGDH having improved pH stability, the modified FADGDH having at least any one of the amino acid substitutions S167P, V551C, (G163K+V551C)

and (G163R+V551C) of SEQ ID No. 2 in the sequence table, or such a substitution at an equivalent position to said positions in an amino acid sequence of another species.

Item 19. A gene coding for a modified FADGDH according to any one of claims 1 to 18.

Item 20. A vector containing the gene according to claim 19.

Item 21. A transformant transformed with the vector according to claim 20.

Item 22. A process for producing a modified FADGDH the process comprising incubating the transformant according to claim 21.

Item 23. A glucose assay kit containing a modified FADGDH according to any one of claims 1 to 18.

Item 24. A glucose sensor containing a modified FADGDH according to any one of claims 1 to 18.

Item 25. A method for measuring glucose, the method comprising a modified FADGDH according to any one of claims 1 to 18.

Item 26. A modified FADGDH having improved heat stability, the modified FADGDH having higher improved substrate specificity than wild-type flavin adenine dinucleotide dependent glucose dehydrogenase (FADGDH) derived from *Aspergillus oryzae* and having an amino acid substitution at position 53 in the amino acid sequence of SEQ ID No. 2 or at an equivalent position to said position in an amino acid sequence.

Item 27. A modified FADGDH according to Item 26, the modified FADGDH having an activity on xylose of 5.0% or less of that on glucose.

Item 28. A modified FADGDH according to Item 26, the modified FADGDH having any one of the amino acid substitutions selected from the group consisting of G53H, G53N, G53K, G53M, G53T, G53V and G53C of SEQ ID No. 2, or at an equivalent position to said positions in an amino acid sequence.

Item 29. A modified FADGDH according to Item 26, the modified FADGDH having an amino acid substitution at at least one position selected from the group consisting of positions 163, 167 and 551 in the amino acid sequence of SEQ ID No. 2, or at an equivalent position to said positions in an amino acid sequence.

Item 30. A modified FADGDH according to Item 29, the modified FADGDH having any one of the amino acid substitutions selected from the group consisting of (G53H+S167P), (G53N+S167P), (G53H+S167P) and (G53N+G163R+V551C) in the amino acid sequence represented by SEQ ID No. 2, or such a substitution at an equivalent position to said positions in an amino acid sequence.

Item 31. A process for producing a modified FADGDH, the process comprising using a gene coding for a modified FADGDH of any one of Items 26 to 30, a vector containing the gene, a transformant transformed with the vector, and incubating the transformant.

Item 32. A glucose assay kit containing a modified FADGDH according to any one of Items 26 to 30.

Item 33. A method for measuring glucose containing a modified FADGDH according to any one of Items 26 to 30.

The modified FADGDH of Item 26 has lower activity on pentose than the wild-type flavin adenine dinucleotide dependent glucose dehydrogenase (FADGDH). An example of pentose includes xylose. The modified FADGDH of Item 26 has activity on xylose of 5.0% or less of that on glucose contrary to the wild-type FADGDH. The activity on xylose refers to the relative ratio % (taking glucose as 1) of the reaction rate when a glucose substrate and a xylose substrate are used.

The modified FADGDH of Item 26 preferably has improved heat stability compared to that of the wild-type flavin adenine dinucleotide dependent glucose dehydrogenase (FADGDH). The modified FADGDH of Item 26 has a residual activity ratio of 20% or higher, preferably 40% or higher, and more preferably 70% or higher, after heat treatment at 50° C. for 15 minutes. When such stability can be maintained, the modified FADGDH can be subjected to a heat-drying treatment during the production process.

The modified FADGDH of Item 26 preferably has improved pH stability compared to that of the wild-type flavin adenine dinucleotide dependent glucose dehydrogenase (FADGDH). The modified FADGDH of Item 26 has a residual activity ratio of 80% or higher after treatment at 25° C. for 16 hours in the pH range from 4.5 to 7.0, or has a residual activity ratio of 80% or higher, and preferably 90% or higher, after treatment at 25° C. for 16 hours in the pH range from 4.5 to 6.5.

Item 34. A modified FADGDH having improved heat stability compared to that of the wild-type flavin adenine dinucleotide dependent glucose dehydrogenase (FADGDH), the modified FADGDH being preferably derived from a eukaryote, more preferably derived from a filamentous fungus, and even more preferably derived from an *Aspergillus* fungus, and having preferably has a residual activity ratio of preferably 20% or higher, more preferably 40% or higher, and even more preferably 80% or higher, after heat treatment at 50° C. for 15 minutes.

Item 35. A modified FADGDH having an amino acid sequence represented by SEQ ID No. 2, the modified FADGDH having the primary structure wherein at least one amino acid is substituted, deleted, inserted or added, and an example being the modified FADGDH having improved heat stability wherein an amino acid is substituted at at least one position selected from the group consisting of positions 120, 160, 162, 163, 164, 165, 166, 167, 170, 171, 172, 180, 329, 331, 369, 471 and 551, in the amino acid sequence of SEQ ID No. 2, or at an equivalent position to said positions in an amino acid sequence of another species. A more preferable example is a modified FADGDH having an amino acid substitution at at least any one of the positions 162, 163, 167 and 551.

Item 37. A modified FADGDH having improved heat stability compared to that of a wild-type flavin adenine dinucleotide dependent glucose dehydrogenase (FADGDH) derived from *Aspergillus oryzae*, the modified FADGDH having an amino acid substitution at position 163, position 551 or positions 163 and 551 in the amino acid sequence of SEQ ID No. 2, or at an equivalent position to said positions in an amino acid sequence.

Item 38. A modified FADGDH according to Item 37, the modified FADGDH having any one of the amino acid substitutions selected from the group consisting of G163D, G163K, G163L, G163R, V551A, V551C, V551T, V551Q, V551S, V551Y, (G163D+S167P), (L165P+V551C), (L165V+V551C), (G163K+V551C), and (G163R+V551C) in the amino acid sequence of SEQ ID No. 2, or having an equivalent amino acid substitution to said substitutions at an equivalent position to said positions in an amino acid sequence.

Item 39. A modified FADGDH having an amino acid substitution at at least any one of the positions, in addition to one of position 163, position 551 or positions 163 and 551, selected from the group consisting of the positions 120, 160, 162, 164, 165, 166, 167, 170, 171, 172, 180, 329, 331, 369 and 471 in the amino acid sequence of SEQ ID No. 2, or at an equivalent position to said positions in an amino acid sequence.

Item 40. A modified FADGDH having improved pH stability compared to that of the wild-type flavin adenine dinucleotide dependent glucose dehydrogenase (FADGDH), the modified FADGDH preferably derived from a eukaryote, more preferably derived from a filamentous fungus, and further preferably derived from an *Aspergillus* fungus.

Item 41. A modified FADGDH having improved pH stability, the modified FADGDH having an amino acid substitution at, in addition to positions 163, 551 or 163 and 551, at position 167 in the amino acid sequence of SEQ ID No. 2, or an equivalent position to said positions in an amino acid sequence.

Item 42. A modified FADGDH according to Item 41, the modified FADGDH having any one of the amino acid substitutions selected from the group consisting of S167P, V551C, (G163K+V551C) and (G163R+V551C) in the amino acid sequence of SEQ ID No. 2, or an equivalent amino acid substitution to said amino acid substitutions at an equivalent position to said positions in an amino acid sequence.

Item 43. An FADGDH according to any one of Items 34 to 42, the FADGDH having a residual activity of 80% or higher, and preferably 90% or higher, after treatment at 25° C. for 16 hours in the pH range from 4.5 to 6.5.

Item 44. A modified FADGDH having improved pH stability, the modified FADGDH having an amino acid substitution at at least one position selected from the group consisting of the positions 163, 167 and 551 of SEQ ID No. 2, or at an equivalent position to said positions in an amino acid sequence of another species.

Item 45. A modified FADGDH having improved pH stability, the modified FADGDH having at least one of the amino acid substitutions S167P, V551C, (G163K+V551C), and (G163R+V551C) of SEQ ID No. 2, or at an equivalent position to said positions in an amino acid sequence of another species.

Item 46. A process for producing a modified FADGDH, the method comprising using a gene coding for a modified FADGDH of any one of Items 34 to 45, a vector containing the gene, a transformant transformed with the vector, and incubating the transformant.

Item 47. A glucose assay kit or a glucose sensor containing a modified FADGDH according to any one of Items 34 to 45.

Item 48. A method for measuring glucose comprising a modified FADGDH according to any one of Items 34 to 45.

In the modified FADGDH of the present invention, particularly the amino acid substitutions G163K, G163L, G163R, S167P, V551A, V551C, V551Q, V551S, V551Y, (G160I+S167P), (S162F+S167P), (S167P+N169Y), (S167P+L171I), (S167P+L171K), (S167P+L171V), (S167P+V172I), (S167P+V172W), (G163K+V551C) and (G163R+V551C) contribute to the improvement of heat stability.

The term "K120E" herein refers to the substitution of K(Lys) at position 120 with E(Glu). Further, the term "(G160E+S167P)" refers to the substitutions of G at position 160 with E, and S at position 167 with P, respectively. The symbol "+" means a multiple variant (double mutant in this example) having both substitutions.

The heat-dryable level is the state in which the residual activity is 20% or higher, preferably 40% or higher, and more preferably 60% or higher, after treatment 50° C. for 15 minutes.

Effects of the Invention

The stability improvement of the FADGDH of the present invention can reduce the heat-inactivation of enzymes that occurs during the production processes of a reagent for measuring glucose, a glucose assay kit and a glucose sensor, thereby decreasing the amount of enzymes used and improving measurement precision.

BEST MODE FOR CARRYING OUT THE INVENTION

Figure 1:
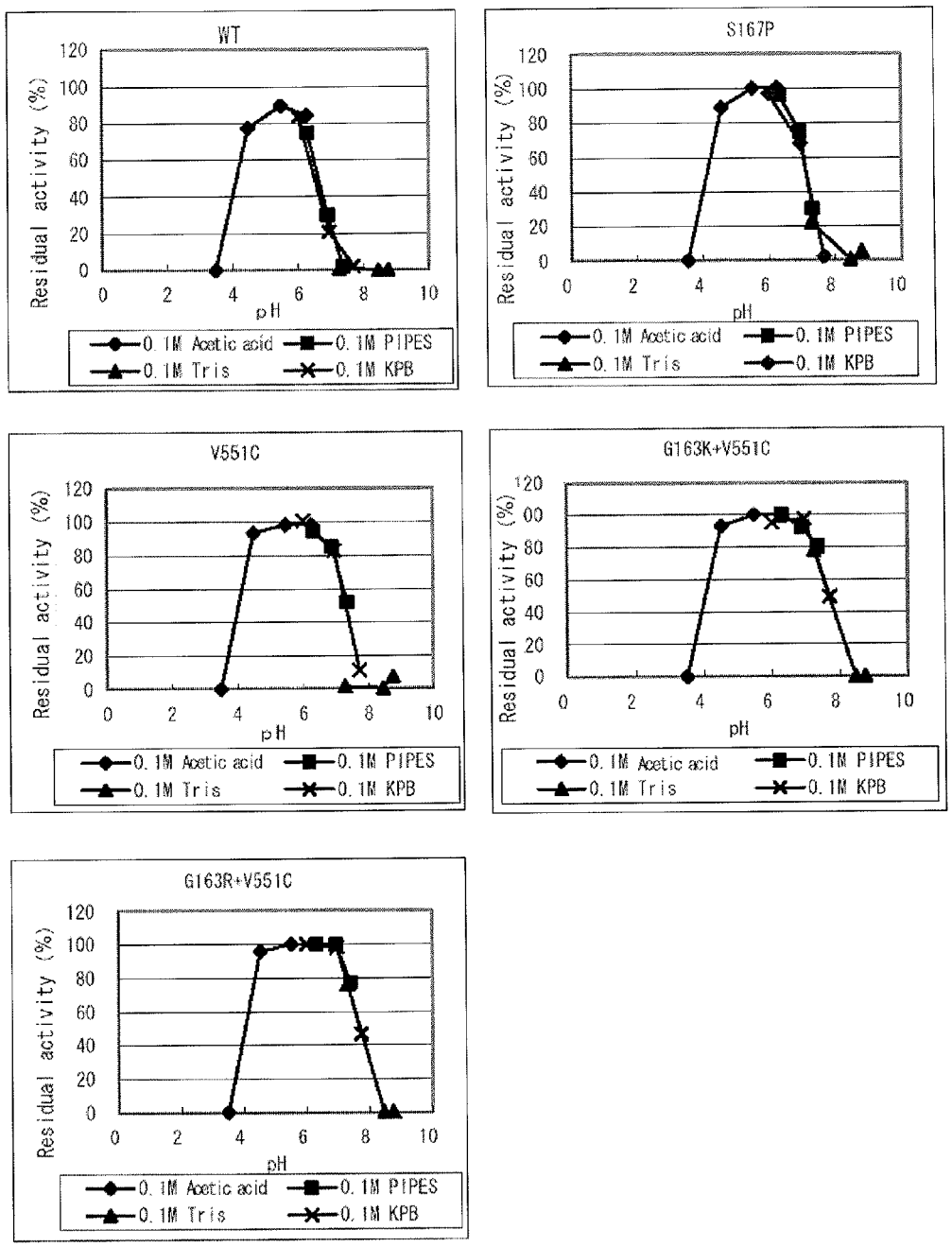
FIG. 1 shows the pH stabilities of purified samples of a wild-type FADGDH derived from *Aspergillus oryzae* and modified FADGDHs. Acetate buffer: pH 3.5 to 6.3, PIPES buffer: pH 6.3 to 7.3, tris chloride buffer: pH 7.3 to 8.8, and phosphate buffer: pH 6.0 to 7.7 were used respectively.

The present invention comprises a modified FADGDH whose heat stability is improved compared to that of a recombinant FADGDH.

Wild-type FADGDH derived from *Aspergillus oryzae* having the amino acid sequence represented by SEQ ID No. 2 was obtained in the following manner.

Using the database available at the National Center for Biotechnology Information (hereinafter referred to as "NCBI"), the present inventors presumed *Aspergillus-oryzae*-derived glucose dehydrogenase gene and obtained it, and found that *Aspergillus-oryzae*-derived glucose dehydrogenase can be obtained using the gene in *E. coli*.

To obtain an *Aspergillus-oryzae*-derived GDH gene, GDH purification of a culture supernatant from an in-house *Aspergillus oryzae* TI strain was attempted using chromatography, but it was difficult to obtain highly purified GDH, and cloning with partial amino acid sequence, one of the common techniques to obtain a gene, had to be abandoned. However, the inventors found that *Penicillium lilacinoechinulatum* NBRC6231 strain can produce GDH, and succeeded in determining a partial amino acid sequence using a purified enzyme. Subsequently, a GDH gene derived from *P. lilacino-echinulatum* NBRC6231 was partially obtained via a PCR method using the determined amino acid sequence, and the base sequence was determined (1356 bp). Finally, based on the base sequence, *Aspergillus oryzae* GDH gene was estimated and obtained. The summary is described in the following Experimental Example 1 and Experimental Example 2.

Experimental Example 1

Estimation of *Aspergillus-oryzae*-derived Glucose Dehydrogenase (hereinafter also referred to as "AOGDH") Gene
1. Obtainment of *Aspergillus-oryzae*-derived GDH A lyophilized sample of an *Aspergillus oryzae* TI strain was inoculated into potato dextrose agar culture medium (product of Difco Laboratories Incorporated) and incubated at 25° C. for renaturation. The renatured hyphae on each plate were recovered together with the agar, and suspended in filter-sterilized water. Six liters of production medium (1% malt extract, 1.5% soybean peptide, 0.1% $MgSO_4$-heptahydrate, 2% glucose, and pH 6.5) was prepared in two 10-liter jar fermenters, sterilized in an autoclave for 15 minutes at 120° C., and allowed to cool. The above cell suspension was inoculated into the medium, and incubated at 30° C. under aerobic conditions while stirring. The incubation was terminated 64 hours after initiation; the cells were removed using filtration to collect a filtrate having GDH activity. The collected supernatant was subjected to ultrafiltration (a molecular weight cutoff of 10000) to remove low molecular weight substances. Then, ammonium sulfate was added and dissolved to give a saturation degree of 60%, and the resulting supernatant was subjected to ammonium sulfate fractionation to recover the GDH-containing supernatant fraction using a centrifuge. The fraction was loaded into an Octyl-Sepharose column and eluted using an ammonium sulfate saturation gradient of 60 to 0% to further recover the fraction with GDH activity. The obtained GDH solution was desalted using a G-25-Sepharose column, and ammonium sulfate having a 60% saturation degree was added and dissolved therein. The resulting solution was adsorbed on a Phenyl-Sepharose column and eluted using an ammonium sulfate saturation gradient of 60 to 0% to recover the fraction having GDH activity. The fraction was further heated at 50° C. for 45 minutes, and subjected to centrifugation to obtain the supernatant. The solution thus obtained by the above steps was used as the purified GDH sample (AOGDH). The buffer solution used in the above purification process was 20 mM potassium phosphate buffer solution (pH6.5). To further determine the partial amino acid sequence of AOGDH, the purification was attempted by various means such as ion exchange chromatography, gel filtration chromatography, and the like. However, a product purified highly enough to determine a partial amino acid sequence was not obtained.

2. Obtainment of GDH Derived from Filamentous Fungus *Penicillium*

Using *Penicillium lilacinoechinulatum* NBRC6231 as a GDH-producing strain derived from filamentous fungus *Penicillium*, incubation and purification were carried out in the same manner as in the aforementioned processes for the *Aspergillus oryzae* TI strain, and a substantially homogenous purified sample was obtained using SDS electrophoresis.

cDNA Production

In accordance with the above process (provided that the incubation time in the jar fermenter was 24 hours) *Penicillium lilacinoechinulatum* NBRC6231 was cultured, and the cells were recovered using filter-paper filtration. The obtained cells were immediately frozen in liquid nitrogen, and disrupted in a cool mill (Toyobo Co., Ltd.). The total RNA was immediately extracted from the disrupted cells using a Sepasol RNA kit (Nacalai Tesque, Inc.), following the manufacturer's protocol. mRNA was purified from the obtained total RNA using Origotex-dt30 (product of Daiichi Pure Chemicals Co., Ltd.), and the purified mRNA was used as a template to perform RT-PCR using ReverTra-Plus-™ (Toyobo Co., Ltd.). The obtained product was subjected to agarose electrophoresis to denature a portion equivalent to a chain length of 0.5 to 4.0 kb. cDNA was extracted and purified from the denatured gel fragment using MagExtractor-PCR&Gel Clean Up (Toyobo Co., Ltd.).

Determination of GDH Gene Partial Sequence

The NBRC6231-derived GDH purified above was dissolved in Tris-HCl buffer (pH6.8) containing 0.1% SDS and 10% glycerol, Glu-specific V8 endoprotease was added thereto to give a final concentration of 10 μg/ml, and the resultant was incubated at 37° C. for 16 hours to facilitate partial decomposition. This sample was subjected to electrophoresis using a gel having an acrylamide concentration of 16% to isolate peptides. The peptide molecules in this gel were transcribed to a PVDF membrane by a semi-dry method using a blot buffer (1.4% glycin, 0.3% tris, and 20% ethanol). The peptides transcribed onto the PVDF membrane were stained with a CBB staining kit (GelCode Blue Stain Reagent, product of Pierce Chemical Company), and two bands were cut out from the stained peptide fragments so as to analyze the internal amino acid sequence using a peptide sequencer. The obtained amino acid sequences were IGGVVDTSLKVYGT (sequence ID No. 37) and WGGGTKQTVRAGKALGGTST (sequence ID No.38). Degenerate primers containing mixed bases were produced based on these sequences, and PCR was performed using NBRC6231-derived cDNA as a template, whereby an amplified product was obtained. Agarose-gel electrophoresis verified that the PCR products had single bands of about 1.4 kb. These bands were cut out, and extracted and purified using MagExtractor-PCR & Gel Clean Up (product of Toyobo Co., Ltd.). The purified DNA fragments were cloned using TArget Clone-Plus-(product of Toyobo Co., Ltd.), and *E. coli* JM109 competent cells (Toyobo Co., Ltd.) were transformed by heat shock using the obtained vector. For colonies in which the insertion was verified using blue/white screening among the transformed clones, plasmids were subjected to miniprep extraction and purification using MagExtractor-Plasmid (Toyobo Co., Ltd.), and the inserted base sequences (1356 bp) were determined using a primer specific to the plasmid sequence.

AOGDH Gene Estimation

Homologies were searched based on the determined base sequences at the "NCBI BLAST" website, (www.ncbi.nlm.nih.gov/BLAST/), and the AOGDH gene sequence was estimated. The amino acids homology between the estimated AOGDH and the GDH partial sequence from *P. lilacinoechinulatum* NBRC6231 was 49%.

Experimental Example 2

Obtainment of *Aspergillus-oryzae*-Derived Glucose Dehydrogenase Gene and Introduction Thereof to *E. coli*

To obtain an AOGDH gene, mRNA was prepared from cells of an *Aspergillus oryzae* TI strain, and cDNA was synthesized. Two oligo DNAs represented by SEQ. ID Nos. 39 and 40 were synthesized. The AOGDH gene was then amplified with the prepared cDNA as a template, using KOD Plus DNA polymerase (product of Toyobo Co., Ltd.). The DNA fragments were digested with restriction enzymes NdeI and BamHI, and inserted into the NdeI-BamHI site of pBluescript (phagemid into which an NdeI site is introduced so that atg of the NdeI recognition sequence corresponds to LacZ translation initiation codon "atg") to construct a recombinant plasmid. Using this recombinant plasmid, *Escherichia coli* DH5α (product of Toyobo Co., Ltd.) was transformed. The plasmid was extracted from the transformant in the standard manner, and the base sequence of the AOGDH gene was determined (SEQ. ID No. 41). As a result, the amino acid residue presumed from the cDNA sequence was revealed to consist of 593 amino acids (SEQ. ID No. 42). GDH appears to have 588 amino acids according to the presumption based on the database, which suggests that the TI strain GDH has a different number of amino acid residues. The sequence of the gene was verified using TI strain genome DNA, and the gene flanking regions were also confirmed using an RACE technique. Further, a recombinant plasmid containing the DNA sequence according to the database was constructed using PCR to similarly obtain transformants. These transformants were incubated in 200 ml of liquid culture medium supplemented with 100 μg/ml of ampicillin (Terrific broth) at 30° C. for 16 hours while shaking. The GDH activities of the disrupted cell suspensions were examined, and it was found that the transformant containing the GDH sequence estimated from the database did not show GDH activity, whereas the transformant containing the GDH sequence derived from the TI strain had a GDH activity of 8.0 U in the cell per ml of the culture solution. The culture supernatant of the *Aspergillus oryzae* TI strain obtained in Test Example 1 had a GDH activity of 0.2 U/ml.

Experimental Example 3

Introduction of *Aspergillus-oryzae*-derived Glucose Dehydrogenase (hereinafter referred to as "AOGDH") Gene to *E. coli*

When taking FADGDH after signal peptide cleavage as mFADGDH, S2 refers to mFADGDH having a single amino acid length extension at the N terminal due to the addition of only M.

PCR was carried out using the oligonucleotide of SEQ ID No.43 as an N-terminal primer in combination with the primer of SEQ ID No.44, and a recombinant plasmid having the DNA sequence (SEQ ID No. 1) coding for S2 was constructed in the same manner, and the transformant was similarly obtained.

The plasmid containing the DNA sequence of the modified FADGDH was subjected to DNA sequencing and reexamined for the accuracy.

The transformant was incubated for 1 to 2 days in a 10-liter jar fermenter loaded with TB culture medium. After recovering cells from each culture phase, the recovered cells were ultrasonically disrupted to investigate GDH activities. The GDH productivity was increased by the deletion of the amino acid sequences that appeared to be signal peptides.

Wild-type FADGDH derived from *Aspergillus terreus* represented by SEQ ID No. 46 was obtained in the following manner.

Experimental Example 4 cDNA Preparation

A lyophilized sample of *Aspergillus terreus* NBRC33026 (purchased from National Institute of Technology and Evaluation) was inoculated into potato dextrose agar culture medium (product of Difco) at 25° C. and renatured. Fifty milliliters of medium containing 1.5% of soybean peptides, 2% glucose and 1% malt extraction, pH 6.5, was prepared in a 500 ml round-bottomed flask. The thus renatured hyphae on a plate were recovered together with the agar, inoculated into medium, and incubated while shaking at 30° C. for 24 hours, whereby the cells were recovered. The obtained cells were immediately frozen in liquid nitrogen, and disrupted in a cool mill (product of Toyobo Co., Ltd.). The total RNA was immediately extracted from the disrupted cells using a Sepasol RNA I kit (product of Nacalai Tesque, Inc.) in accordance with the manufacturer's protocol. With the total RNA as a template, cDNA was prepared via RT-PCR using ReverTra-Plus-™ (product of Toyobo Co., Ltd.).

Experimental Example 5

GDH Gene Sequencing

The inventors have succeeded in cloning GDH genes derived from *Aspergillus oryzae, Penicillium lilacinoechinulatum*, and *Penicillium italicum*, and obtained the base sequence information thereof. To clone GDH gene from *Aspergillus terreus*, the presumed GDH amino acid sequences of the above three species were aligned, and degenerate primers were designed based on sequences at highly homologous regions. The genomic DNA prepared in Experimental Example 4 was subjected to PCR, and the amplified products were observed. The amplified products were subcloned to determine the base sequences thereof. Based on the determined GDH partial sequences, the amino acid sequences in the flanking regions at the 5'-end and the 3'-end were determined using an RACE technique. The sequence from the initiation codon to the translation stop codon in the determined gene region is represented by SEQ ID No. 45, and the amino acid sequence estimated therefrom is represented by SEQ ID No. 46. The coenzyme bound glucose dehydrogenase derived from *Aspergillus terreus* FERM BP-08578 disclosed in Patent Document 1 has a very high amino acid homology of about 98.5%, and appears to be substantially equal to the sequence of SEQ ID No. 46. In related fields, the term "homology" refers to, when two amino acid sequences are aligned using a known mathematical algorithm, the proportion (%) of the same amino acid residues in all overlapped amino acids in the optimal alignment (the algorithm used is preferably one by which gaps can be introduced to one or both sequences to optimize the alignment). Examples of such algorithms are shown in Non-patent Literature 1 to 4, but not limited thereto.

Non-Patent Literature 1

Karlin et al., Proc. Natl. Acad. Sci. USA (1993) Vol. 90 p 5873-5877

Non-Patent Literature 2

Needleman et al., J. Mol. Biol. (1970) Vol. 48 p 444-453

Non-Patent Literature 3

Myers and Miller, CABIOS Vol. 4 p 11-17

Non-Patent Literature 4

Pearson et al., Proc. Natl. Acad. Sci. USA (1988) Vol. 85 p 2444-2448

Experimental Example 6

Production of GDH Recombinant Plasmid and GDH Recombinant

A signal peptide was predicted for the amino acid sequence coded by the DNA sequence of SEQ ID No.45, using Signal P3.0 Server. Based on this result, 25 codons were deleted from the N-terminal sequence to remove the signal peptide, and PCR primers (SEQ ID Nos.47 and 48) were produced so that the sequence with the initiation codon (ATG) added thereto would be amplified. Using these primers, the gene amplification was carried out with KOD Plus DNA polymerase (product of Toyobo Co., Ltd.) using NBRC33026 cDNA as a template. The amplified fragments were digested with restriction enzymes NdeI and BamHI, and inserted into the NdeI-BamHI site of pBluescript to which the NdeI site is introduced so that ATG of NdeI recognition sequence corresponds to LacZ translation initiation codon "ATG") to construct recombinant plasmid (pAtGDH-s2-7). *Escherichia coli* DH5a (product of Toyobo Co., Ltd.) was transformed using this recombinant plasmid to obtain *Aspergillus terreus*-derived GDH recombinant. The transformant was incubated while shaking in 200 ml of liquid culture medium (Terrifc Broth) supplemented with 100 µg/ml of ampicillin at 30° C. for 16 hours. The disrupted cell suspension was examined for GDH activity, and the cells had 1.0 U of GDH activity per ml of the culture solution.

The modified FADGDH of the present invention can be obtained by substituting an amino acid at any one of the aforementioned positions in the amino acid sequences of SEQ ID No.2 or SEQ ID No. 46.

For example, "a position equivalent to the position in the amino acid sequence represented by SEQ ID No.2" means the position in other amino acid sequences than that represented by SEQ ID NO.2 equivalent to a position in the sequence represented by SEQ ID NO.2 when the amino acid sequence of SEQ ID No.2 is aligned with said other amino acid sequences homologous, (preferably 60% or higher homologous, more preferably 80% or higher, and further preferably 90% or higher), to those of SEQ ID No. 2.

Examples of the modified FADGDH with improved substrate specificity and/or heat stability provided by the present invention include those having an amino acid substitution at at least one of the positions 53, 163, 167 and 551 in the amino acid sequence of SEQ ID No. 2.

Other examples of the modified FADGDH include those having an amino acid substitution selected from the group consisting of G53H, G53N, G53K, G53M, G53T, G53V, G53C, G163R, S167P, and V551C in the amino acid sequence of SEQ ID No. 2.

The term "G53H" herein refers to the substitution of G(Gly) at position 53 with (His). In particular, the amino acid substitutions G53H, G53N, G53K, G53M, G53T, G53V, and G53C impart substrate specificity improvement to the modified FADGDH. The amino acid substitutions G53H+S167P, G53N+S167P, G53N+G163R+V551C impart improvement of substrate specificity and/or stability to the modified FADGDH.

Examples of the modified FADGDH having improved heat stability of the present invention include those having an amino acid substitution at at least one of the positions 120, 160, 162, 163, 164, 165, 166, 167, 169, 170, 171, 172, 180, 329, 331, 369, 471 and 551. Among the above, the modified FADGDH having an amino acid substitution at at least one of the positions 162, 163, 167 and 551 is preferable.

Specific examples of the modified FADGDH include those having an amino acid substitution selected from the group consisting of K120E, G160E, G160I, G160P, G160S, G160Q, S162A, S162C, S162D, S162E, S162F, S162H, S162L, S162P, G163D, G163K, G163L, G163R, S164F, S164T, S164Y, L165A, L165I, L165N, L165P, L165V, A166C, A166I, A166K, A166L, A166M, A166P, A166S, S167A, S167P, S167R, S167V, N169K, N169P, N169Y, N169W, L170C, L170F, S171I, S171K, S171M, S171Q, S171V, V172A, V172C, V172E, V172I, V172M, V172S, V172W, V172Y, A180G, V329Q, A331C, A331D, A331I, A331K, A331L, A331M, Q331V, K369R, K471R, V551A, V551C, V551T, V551Q, V551S, and V551Y in the amino acid sequence of SEQ ID No.2

The term "K120E" herein means the substitution of K(Lys) at position 120 with E(Glu).

In particular, the amino acid substitutions G163K, G163L, G163R, S167P, V551A, V551C, V551Q, V551S, V551Y, (G160I+S167P), (S162F+S167P), (S167P+N169Y), (S167P+L171I), (S167P+L171K), (S167P+L171V), (S167P+V172I), (S167P+V172W), (G163K+V551C) and (G163R+V551C) facilitate heat stability improvement of the modified FADGDH.

Other examples of the modified FADGDH are those having an amino acid substitution at at least any one of positions 116, 159, 161, 164, 166, 167, 175, 325, 327, 365 and 547 in the amino acid sequence of SEQ ID No.46.

Preferable examples of the modified FADGDH are those having an amino acid substitution selected from the group consisting of K116D, K116G, K116L, K116F, K116Q, Q159A, Q159K, Q159N, Q159P, Q159V, Q159L, E161C, N164Y, N164V, N164C, T166F, T166Y, T166W, T167L, T167V, T167S, G175K, S325A, S325G, S325K, S325Q, S325R, S325T, S325V, S325Y, S327E, Q365R, V547S, V547C, V547A, and V547Q in the amino acid sequence of SEQ ID No.46.

The term "K116D" herein means the substitution of K(Lys) at position 116 with D(Asp).

The process for producing the modified FADGDH in which wild-type *Aspergillus-oryzae*-derived FADGDH having the amino acid sequence represented by SEQ ID No.2 is modified, or the modified FADGDH in which wild-type *Aspergillus-terreus*-derived FADGDH having the amino acid sequence represented by SEQ ID No.46 is modified, is not limited, and they can be produced by the following processes. A technique commonly performed to modify genetic information can be employed to modify the amino acid sequence constituting FADGDH. More specifically, DNA having the genetic information to produce modified proteins can be produced by changing a specific base, or by inserting or deleting a specific base, in DNA having genetic information for protein production. Examples of specific methods for changing a base sequence in DNA include the use of commercial kits (e.g., Transformer Mutagenesis Kit, product of Clontech; EXOIII/Mung Bean Deletion Kit, product of Stratagene; Quick Change Site Directed Mutagenesis Kit, product of Stratagene; etc.) and the employment of PCR.

The produced DNA having the genetic information for producing modified FADGDH is transfected into a host microorganism while being connected to the plasmid, and becomes a transformant for producing the modified FADGDH. Examples of usable plasmids at this stage include *Escherichia coli* JM109, *Escherichia coli* DH5, *Escherichia coli* W3110, *Escherichia coli* C600, etc. A recombinant vector may be transfected into a host microorganism using a method employed for transfecting a recombinant DNA in the presence of calcium ions when, for example, the host microorganism is of *Escherichia coli*. Further, an electroporation method may be used. Furthermore, commercial competent cells (e.g., Competent High JM109: product of Toyobo Co., Ltd.) may be used.

The thus obtained microorganism, i.e., transformant, is capable of stably producing a large amount of the modified FADGDH by being cultured in a nutrient broth. The culture conditions of the transformant host microorganism may be selected considering the nutritional and physiological properties of the host microorganism. Liquid culture is most typically employed; however, aerobic incubation while stirring is industrially advantageous. A wide variety of nutrients typically used for culturing microorganisms can also be used in the culture medium. Any carbon source in the form of an assimilatable carbon compound may be used, and usable examples include glucose, sucrose, lactose, maltose, molasses, pyruvic acid, and the like. Any nitrogen source in the usable form of a nitrogen compound may be acceptable, and usable examples include peptones, meat extracts, yeast extracts, casein hydrolysate, soybean cake alkali hydrolysate, and the like. Other example of nutrients usable as necessary include phosphates, carbonates, sulfates, magnesium, calcium, potassium, iron, manganese, zinc, and like salts; certain amino acids; certain vitamins; etc. The medium temperature can be suitably varied in the range in which cells grow and produce the modified FADGDH. When *Escherichia coli* is used, the temperature is preferably in the range from about 20 to about 42° C. The incubation temperature somewhat varies depending on the conditions; however, the incubation is terminated at a suitable time when the modified FADGDH reaches maximum yield, typically in about 6 to 48 hours. The medium pH can be suitably varied in the range in which cells grow and produce the modified proteins, particularly preferably in the pH ranges from 6.0 to 9.0.

The culture solution containing the modified-FADGDH-producing cells in the culture may be collected and used without further treatment; however, when the modified FADGDH is present in the culture solution, the solution is typically used after the solution containing the modified proteins and the microorganism cells are separated using a routine method such as filtration, centrifugation, etc. When the modified proteins are present within the cells, the cells are recovered from the obtained culture using a method such as filtration, centrifugation, etc., the recovered cells are then disrupted mechanically or enzymatically using an enzyme such as lysozyme, etc, and a chelating agent such as EDTA, etc., or a surfactant is further added as necessary to solubilize the modified FADGDH, thereby isolating and collecting the modified proteins in the form of a solution.

The thus obtained modified FADGDH-containing solution may be subjected to precipitation by, for example, concentration under reduced pressure, membrane concentration, salting out using ammonium sulfate or sodium sulfate, or a fractional precipitation with a hydrophilic solvent such as methanol, ethanol, acetone, etc. Heat treatment and isoelectric treatment are alternative, effective precipitation methods. The purified modified FADGDH can be obtained using gel filtration with an adsorbent or gel filtering agent, adsorption chromatography, ion exchange chromatography, or affinity chromatography.

Glucose Assay Kit

The present invention further comprises a glucose assay kit containing the modified FADGDH according to the present invention. The glucose assay kit of the present invention contains a sufficient amount of the modified FADGDH of the invention for at least a single assay. In addition to the modified FADGDH of the invention, the kit typically consists of an assay buffer solution, a mediator, a glucose standard solution for forming a calibration curve, and guidelines for use. The modified FADGDH of the present invention can be provided in various forms such as a lyophilized reagent, a solution preserved in a suitable solution, etc.

Glucose Sensor

Furthermore, the present invention comprises a glucose sensor that uses the modified FADGDH of the invention. Usable electrodes include carbon electrodes, gold electrodes, platinum electrodes, or the like, and the enzyme of the present invention is immobilized thereon. The enzyme may be immobilized via a method that uses a crosslinking reagent; a method in which the enzyme is encapsulated in a polymer matrix; a method in which the enzyme is coated with a dialyzer; a method that uses a crosslinking polymer, an electric conductive polymer, a redox polymer, or the like, in which the enzyme may be immobilized together with a representative electron mediator such as ferrocene or derivatives thereof; the enzyme may be adsorbed and immobilized on the electrode; or these methods may be used in combination. The modified FADGDH of the present invention is typically immobilized on the electrode using glutaraldehyde, which is then blocked with an amine reagent.

Glucose concentration can be measured as follows. A buffer solution is placed in a thermostat, and a constant temperature is maintained. A mediator such as potassium ferricyanide, phenazine methosulfate, or the like can be used. The electrode on which the modified FADGDH of the present invention is immobilized is used as a working electrode, and a counter electrode (e.g., a platinum electrode) and a reference electrode (e.g., Ag/AgCl electrode) are used. A constant voltage is applied to a carbon electrode, and a sample containing glucose is added thereto once the steady current is achieved, whereby the increased current is measured. The glucose concentration in the sample can be calculated based on a calibration curve created using a glucose solution with a standard concentration.

In the present invention, FAD-dependent GDH activity was measured under the following conditions.

Test Example

Reagent
50 mM PIPES buffer solution pH6.5 (including 0.1% Triton X-100),
163 mM PMS solution,
6.8 mM 2,6-dichlorophenol indophenol (DCPIP) solution,
1M D-glucose solution, 15.6 ml of the aforementioned PIPES buffer, 0.2 ml of DCPIP solution and 4 ml of D-glucose were mixed to make the reaction reagent.

Measurement Conditions 2.9 ml of the reaction reagent was pre-heated for 5 minutes at 37° C. 0.1 ml of GDH solution was added and slowly mixed. A spectrometer was calibrated for 5 minutes at 37° C. at 600 nm using water as a reference. The absorbance change per minute ($\Delta OD_{TEST}$) was determined from the linear portion. As a blank test, the absorbance change per minute ($\Delta OD_{BLANK}$) was determined in the same manner as above except that a solvent of the GDH solution was added to the reagent in place of the GDH solution. From the values thus obtained, the GDH activity was calculated by the following equation. In the present invention, one unit (U) of the GDH activity was defined as the amount of enzyme that reduces 1 μmol of DCPIP per minute in the presence of 200 mM D-glucose.

$$\text{Activity (U/ml)} = \{-(\Delta OD_{TEST} - \Delta OD_{BLANK}) \times 3.0 \times \text{dilution ratio}\} / \{16.3 \times 0.1 \times 1.0\}$$

In the equation, 3.0 is the amount (ml) of reaction reagent+enzyme solution, 16.3 is the millimolar molecular absorption coefficient ($cm^2$/micromole) under the conditions for measuring activities of the present invention, 0.1 is the amount of enzyme solution (ml) and 1.0 is the optical light path (cm) of the cell.

Example 1

Examination of Heat Stability of Modified FADGDH Using the Glucose Measurement System This was done according to the methods for measuring FADGDH activity as described in Test Example above.

First, 50 ml of the *Aspergillus oryzae*- or *Aspergillus tereus*-derived FADGDH dissolved to about 20 U/ml in enzyme diluent (50 mM potassium phosphate buffer (pH 5.5), 0.1% Triton X-100) was prepared. Per each modified FADGDH, two samples consisting of 1.0 ml of this enzyme solution were prepared. Per each modified FADGDH, two 0.1 ml controls were prepared in the same way as above except that water was added in place of each modified FADGDH.

Of the two samples, one was stored at 4° C., while the other was incubated at 50° C. for 15 minutes. After the treatment, each sample was measured for FADGDH activity. Enzyme activity after stored at 4° C. was given as 100, and each of the activity values after 15 minute incubation at 50° C. were compared and given as residual activity ratios (%).

Example 2

Introduction of Mutation into FADGDH Gene Derived from *Aspergillus oryzae*

After transforming commercially-available *Escherichia coli* competent cells (*E. coli* DH5; product of Toyobo Co., Ltd.) using the recombinant plasmid pAOGDH-S2 that contains a gene encoding the wild type FADGDH (SEQ ID NO:

1), the transformants were inoculated into liquid culture medium (1% polypeptone, 0.5% yeast extract, 0.5% NaCl; pH7.3) containing ampicillin (50 µg/ml; product of Nacalai Tesque, Inc.) followed by shaking culture at 30° C. overnight. From the overnight culture, the plasmid was prepared according to a standard method. Using the plasmid as a template, mutations were introduced using the Diversify™ PCR Random Mutagenesis Kit (product of Clontech) according to the instructions. The modified FADGDH mutant plasmids that have the ability to produce glucose dehydrogenase were prepared according to the above method.

Example 3

Preparation of Crude Enzyme Solutions Including Modified FADGDHs Derived from *Aspergillus oryzae*

After transforming commercially-available *Escherichia coli* competent cells using the plasmids prepared in Example 2, the transformants were applied onto agar medium (1% polypeptone, 0.5% yeast extract, 0.5% NaCl, 1.5% agar; pH7.3) containing ampicillin, and then subjected to shaking culture at 30° C. overnight. Colonies obtained from the overnight culture were further inoculated into LB liquid culture medium containing ampicillin (100 µg/ml), and then subjected to shaking culture at 30° C. overnight. Part of the culture solution was centrifuged to collect the cells, and homogenized in 50 mM phosphate buffer solution (pH7.0) using glass beads so as to prepare crude enzyme solution.

Example 4

Screening of Mutants with Improved Heat Stability

Using the crude enzyme solutions prepared as in Example 3, glucose dehydrogenase activities were measured according to the above measuring method. After heating the crude enzyme solutions at 50° C. for 15 minutes, glucose dehydrogenase activities were measured, and 3 types of mutants with improved heat stability were obtained. Plasmids encoding these 3 types of mutants were named as pAOGDH-M1, pAOGDH-M2, pAOGDH-M3 and pAOGDH-M4.

To identify the positions of the mutations in pAOGDH-M1, pAOGDH-M2, pAOGDH-M3 and pAOGDH-M4, base sequences of the gene encoding glucose dehydrogenase were determined using a DNA sequencer (ABI PRISM™ 3700DNA Analyzer, PerkinElmer Co., Ltd.). As a result, substitutions of serine to proline at position 162 of SEQ ID NO: 2 in pAOGDH-M1, serine to proline at position 167 and lysine to arginine at position 471 in pAOGDH-M2, alanine to glycine at position 180 and valine to alanine at position 551 in pAOGDH-M3, lysine to glutamic at position 120, serine to proline at position 167, and lysine to arginine at position 369 in pAOGDH-M4 are confirmed. The results are shown in Table 1.

TABLE 1

| Position of Amino Acid Substitution | Heat Stability (%) |
| --- | --- |
| S162P | 38.1 |
| S167P + K471R | 41.8 |
| A180G + V551A | 41.9 |
| K120E + S167P + K369R | 64.2 |
| Wild Type | 19.5 |

Mutagenesis was performed using a QuickChange™ Site-Directed Mutagenesis Kit (product of Stratagene) according to the instructions to make modified mutant FADGDH plasmids having the ability to produce glucose dehydrogenase. Plasmid pAOGDH-S2 was used as a template. For the primer sets, a synthetic oligonucleotide of SEQ ID NO: 3 designed to have several sorts of amino acids substituting glycine at position 160 and the complementary synthetic oligonucleotide thereof, a synthetic oligonucleotide of SEQ ID NO: 4 designed to have several sorts of amino acids substituting tryptophan at position 161 and the complementary synthetic oligonucleotide thereof, a synthetic oligonucleotide of SEQ ID NO: 5 designed to have several sorts of amino acids substituting serine at position 162 of and the complementary synthetic oligonucleotide thereof, a synthetic oligonucleotide of SEQ ID NO: 6 designed to have several sorts of amino acids substituting glycine at position 163 and the complementary synthetic oligonucleotide thereof, a synthetic oligonucleotide of SEQ ID NO: 7 designed to have several sorts of amino acids substituting serine at position 164 and the complementary synthetic oligonucleotide thereof, a synthetic oligonucleotide of SEQ ID NO: 8 designed to have several sorts of amino acids substituting leucine at position 165 and the complementary synthetic oligonucleotide thereof, a synthetic oligonucleotide of SEQ ID NO: 9 designed to have several sorts of amino acids substituting alanine at position 166 and the complementary synthetic oligonucleotide thereof, a synthetic oligonucleotide of SEQ ID NO: 10 designed to have several sorts of amino acids substituting serine at position 167 and the complementary synthetic oligonucleotide thereof, a synthetic oligonucleotide of SEQ ID NO: 11 designed to have several sorts of amino acids substituting glycine at position 168 and the complementary synthetic oligonucleotide thereof, a synthetic oligonucleotide of SEQ ID NO: 12 designed to have several sorts of amino acids substituting asparagine at position 169 and the complementary synthetic oligonucleotide thereof, a synthetic oligonucleotide of SEQ ID NO: 13 designed to have several sorts of amino acids substituting leucine at position 170 and the complementary synthetic oligonucleotide thereof, a synthetic oligonucleotide of SEQ ID NO: 14 designed to have several sorts of amino acids substituting serine at position 171 and the complementary synthetic oligonucleotide thereof, a synthetic oligonucleotide of SEQ ID NO: 15 designed to have several sorts of amino acids substituting valine at position 172 and the complementary synthetic oligonucleotide there a synthetic oligonucleotide of SEQ ID NO: 16 designed to have several sorts of amino acids substituting valine at position 329 and the complementary synthetic oligonucleotide thereof, a synthetic oligonucleotide of SEQ ID NO: 17 designed to have several sorts of amino acids substituting leucine at position 330 and the complementary synthetic oligonucleotide thereof, a synthetic oligonucleotide of SEQ ID NO: 18 designed to have several sorts of amino acids substituting alanine at position 331 and the complementary synthetic oligonucleotide thereof, and a synthetic oligonucleotide of SEQ ID NO: 19 designed to have several sorts of amino acids substituting valine at position 551 and the complementary synthetic oligonucleotide thereof are used. The plasmids obtained were further prepared in the same manner as in the above method.

After the transformation of commercially-available *Escherichia coli* competent cells (*E. coli* DH5; product of Toyobo Co., Ltd.), using the plasmid prepared as in Example 4, crude enzyme solutions were prepared as in the same manner as in Example 3.

Using the above crude enzyme solutions, glucose dehydrogenase activities were measured according to the above method for measuring glucose dehydrogenase activities. Glucose dehydrogenase activities were also measured after heating the crude enzyme solutions at 50° C. for 15 minutes. As a result, 16 sorts of mutants with improved heat stability were obtained. Plasmids encoding these 16 sorts of the mutants were named as pAOGDH-M4, pAOGDH-M5, pAOGDH-M6, pAOGDH-M7, pAOGDH-M8, pAOGDH-M9, pAOGDH-M10, pAOGDH-M11, pAOGDH-M12, pAOGDH-M13, pAOGDH-M14, pAOGDH-M15, pAOGDH-M16, pAOGDH-M17, pAOGDH-M18, and AOGDH-M19.

In order to identify the mutation sites in pAOGDH-M4, pAOGDH-M5, pAOGDH-M6, pAOGDH-M7, pAOGDH-M8, pAOGDH-M9, pAOGDH-M10, pAOGDH-M11, pAOGDH-M12, pAOGDH-M13, pAOGDH-M14, pAOGDH-M15, pAOGDH-M16, pAOGDH-M17, pAOGDH-M18, and pAOGDH-M19, base sequences of the genes encoding glucose dehydrogenase were determined using a DNA sequencer (product of ABI PRISM™ 3700DNA Analyzer; PerkinElmer Co., Ltd.). As a result, the substitutions of glycine with proline at position 160 of SEQ ID NO: 2 in pAOGDH-M5, glycine with lysine at position 163 in pAOGDH-M6, glycine with leucine at position 163 in pAOGDH-M7, glycine with arginine at position 163 in pAOGDH-M8, serine with alanine at position 167 in pAOGDH-M9, serine with proline at position 167 in pAOGDH-M10, serine with arginine at position 167 in pAOGDH-M11, serine with valine at position 167 in pAOGDH-M12, serine with proline at position 171 in pAOGDH-M13, valine with alanine at position 551 in pAOGDH-M14, valine with cysteine at position 551 in pAOGDH-M15, valine with threonine at position 551 in pAOGDH-M16, valine with glutamine at position 551 in pAOGDH-M17, valine with serine at position 551 in pAOGDH-M18, valine with tyrosine at position 551 in pAOGDH-M19 were identified. The results are shown in Table 2.

TABLE 2

| Positions of Amino Acid Mutations | Heat Stability % |
|---|---|
| G160P | 21.4 |
| G163K | 56.1 |
| G163L | 54.5 |
| G163R | 51.2 |
| S167A | 38.1 |
| S167P | 49.8 |
| S167R | 21.4 |
| S167V | 23.4 |
| S171P | 21.4 |
| V551A | 60.5 |
| V551C | 61.3 |
| V551T | 36.8 |
| V551Q | 40.8 |
| V551S | 41.3 |
| V551Y | 46.5 |
| Wild Type | 19.5 |

Example 5

Construction of Mutant Plasmids with Multiple Mutations and Heat Stability

Mutagenesis was performed using a QuickChange™ Site-Directed Mutagenesis Kit (product of Stratagene) according to the instructions to make modified FADGDH mutant plasmids having the ability to produce glucose dehydrogenase. The plasmid pAOGDH-M10 was used as a template. For primer sets, a synthetic oligonucleotide of SEQ ID NO: 20 designed to have several sorts of amino acids substituting glycine at position 160 and the complementary synthetic oligonucleotide thereof, a synthetic oligonucleotide of SEQ ID NO: 21 designed to have several sorts of amino acids substituting tryptophan at position 161 and the complementary synthetic oligonucleotide thereof, a synthetic oligonucleotide of SEQ ID NO: 22 designed to have several sorts of amino acids substituting serine at position 162 and the complementary synthetic oligonucleotide thereof, a synthetic oligonucleotide of SEQ ID NO: 23 designed to have several sorts of amino acids substituting glycine at position 163 and the complementary synthetic oligonucleotide thereof, a synthetic oligonucleotide of SEQ ID NO: 24 designed to have several sorts of amino acids substituting serine at position 164 and the complementary synthetic oligonucleotide thereof, a synthetic oligonucleotide of SEQ ID NO: 25 designed to have several sorts of amino acids substituting leucine to several sorts of amino acids at position 165 and the complementary synthetic oligonucleotide thereof, a synthetic oligonucleotide of SEQ ID NO: 26 designed to have several sorts of amino acids substituting alanine at position 166 and the complementary synthetic oligonucleotide thereof, a synthetic oligonucleotide of SEQ ID NO: 27 designed to have several sorts of amino acids substituting glycine at position 168 and the complementary synthetic oligonucleotide thereof, a synthetic oligonucleotide of SEQ ID NO: 28 designed to have several sorts of amino acids substituting asparagine to several sorts of amino acids at position 169 and the complementary synthetic oligonucleotide thereof, a synthetic oligonucleotide of SEQ ID NO: 29 designed to have several sorts of amino acids substituting leucine to several sorts of amino acids at position 170 and the complementary synthetic oligonucleotide thereof, a synthetic oligonucleotide of SEQ ID NO: 30 designed to have several sorts of amino acids substituting serine to several sorts of amino acids at position 171 and the complementary synthetic oligonucleotide thereof, a synthetic oligonucleotide of SEQ ID NO: 31 designed to have several sorts of amino acids substituting valine to several sorts of amino acids at position 172 and the complementary synthetic oligonucleotide thereof, a synthetic oligonucleotide of SEQ ID NO: 32 designed to have several sorts of amino acids substituting valine to several sorts of amino acids at position 329 and the complementary synthetic oligonucleotide thereof, a synthetic oligonucleotide of SEQ ID NO: 33 designed to have several sorts of amino acids substituting leucine to several sorts of amino acids at position 330 and the complementary synthetic oligonucleotide thereof, a synthetic oligonucleotide of SEQ ID NO: 34 designed to have several sorts of amino acids substituting alanine to several sorts of amino acids at position 331, valine to several sorts of amino acids at position 551 a synthetic oligonucleotide of SEQ ID NO: 35 designed to have several sorts of amino acids substituting and the complementary synthetic oligonucleotide thereof are used. The obtained plasmids were prepared in the same manner as in the above method.

Mutagenesis is performed using QuickChange™ Site-Directed Mutagenesis Kit (product of Stratagene) according to the instructions to make modified FADGDH mutant plasmids having the ability to produce glucose dehydrogenase. Plasmid pAOGDH-M15 was used as a template, and a synthetic oligonucleotide of SEQ ID NO: 36 designed to have several sorts of amino acids substituting glycine at position 163 and the complementary synthetic oligonucleotide thereof were used as a primer set. The obtained plasmid was prepared in the same manner as in the above method.

After transforming commercially available *Escherichia coli* competent cells (*E. coli* DH5; product of Toyobo Co., Ltd.) using plasmids prepared in Example 4, crude enzyme solutions were prepared in the same manner as in Example 3.

Using the above crude enzyme solutions, glucose dehydrogenase activities were measured according to the above method for measuring glucose dehydrogenase activities. After heating the crude enzyme solutions at 50° C. for 15 minutes, glucose dehydrogenase activities were measured. As a result, 57 sorts of mutants with improved heat stability were obtained. Plasmids encoding these 57 sorts of mutants were named as pAOGDH-M20, pAOGDH-M21, pAOGDH-M22, pAOGDH-M23, pAOGDH-M24, pAOGDH-M25, pAOGDH-M26, pAOGDH-M27, pAOGDH-M28, pAOGDH-M29, pAOGDH-M30, pAOGDH-M31, pAOGDH-M32, pAOGDH-M33, pAOGDH-M34, pAOGDH-M35, pAOGDH-M36, pAOGDH-M37, pAOGDH-M38, pAOGDH-M39, pAOGDH-M40, pAOGDH-M41, pAOGDH-M42, pAOGDH-M43, pAOGDH-M44, pAOGDH-M45, pAOGDH-M46, pAOGDH-M47, pAOGDH-M48, pAOGDH-M49, pAOGDH-M50, pAOGDH-M51, pAOGDH-M52, pAOGDH-M53, pAOGDH-M54, pAOGDH-M55, pAOGDH-M56, pAOGDH-M57, pAOGDH-M58, pAOGDH-M59, pAOGDH-M60, pAOGDH-M61, pAOGDH-M62, pAOGDH-M63, pAOGDH-M64, pAOGDH-M65, pAOGDH-M66, pAOGDH-M67, pAOGDH-M68, pAOGDH-M69, pAOGDH-M70, pAOGDH-M71, pAOGDH-M72, pAOGDH-M73, pAOGDH-M74, pAOGDH-M75, and pAOGDH-M76.

In order to identify the mutation sites in pAOGDH-M20, pAOGDH-M21, pAOGDH-M22, pAOGDH-M23, pAOGDH-M24, pAOGDH-M25, pAOGDH-M26, pAOGDH-M27, pAOGDH-M28, pAOGDH-M29, pAOGDH-M30, pAOGDH-M31, pAOGDH-M32, pAOGDH-M33, pAOGDH-M34, pAOGDH-M35, pAOGDH-M36, pAOGDH-M37, pAOGDH-M38, pAOGDH-M39, pAOGDH-M40, pAOGDH-M41, pAOGDH-M42, pAOGDH-M43, pAOGDH-M44, pAOGDH-M45, pAOGDH-M46, pAOGDH-M47, pAOGDH-M48, pAOGDH-M49, pAOGDH-M50, pAOGDH-M51, pAOGDH-M52, pAOGDH-M53, pAOGDH-M54, pAOGDH-M55, pAOGDH-M56, pAOGDH-M57, pAOGDH-M58, pAOGDH-M59, pAOGDH-M60, pAOGDH-M61, pAOGDH-M62, pAOGDH-M63, pAOGDH-M64, pAOGDH-M65, pAOGDH-M66, pAOGDH-M67, pAOGDH-M68, pAOGDH-M69, pAOGDH-M70, pAOGDH-M71, pAOGDH-M72, pAOGDH-M73, pAOGDH-M74, pAOGDH-M75, and pAOGDH-M76, base sequences of the genes encoding glucose dehydrogenase were determined using a DNA sequencer (ABI PRISM™ 3700DNA Analyzer; PerkinElmer Co., Ltd.). As a result, substitutions of glycine with glutamic acid at position 160 and serine with proline at position 167 of SEQ ID NO: 2 in pAOGDH-M20, glycine with isoleucine at position 160 and serine with proline at position 167 in pAOGDH-M21, glycine with serine at position 160 and serine with proline at position 167 in pAOGDH-M22, glycine with glutamine at position 160 and serine with proline at position 167 in pAOGDH-M23, serine with alanine at position 162 and serine with proline at position 167 in pAOGDH-M24, serine with cysteine at position 162 and serine with proline at position 167 in pAOGDH-M25, serine with aspartic acid at position 162 and serine with proline at position 167 in pAOGDH-M26, serine with glutamic acid at position 162 and serine with proline at position 167 in pAOGDH-M27, serine with phenylalanine at position 162 and serine with proline at position 167 in pAOGDH-M28, serine with histidine at position 162 and serine with proline at position 167 in pAOGDH-M29, serine with leucine at position 162 and serine with proline at position 167 in pAOGDH-M30, glycine with aspartic acid at position 163 and serine with proline at position 167 in pAOGDH-M31, serine with phenylalanine at position 164 and serine with proline at position 167 in pAOGDH-M32, serine with threonine at position 164 and serine with proline at position 167 in pAOGDH-M33, serine with tyrosine at position 164 and serine with proline at position 167 in pAOGDH-M34, leucine with alanine at position 165 and serine with proline at position 167 in pAOGDH-M35, leucine with isoleucine at position 165 and serine with proline at position 167 in pAOGDH-M36, leucine with asparagine at position 165 and serine with proline at position 167 in pAOGDH-M37, leucine with proline at position 165 and serine with proline at position 167 in pAOGDH-M38, leucine with valine at position 165 and serine with proline at position 167 in pAOGDH-M39, alanine with cysteine at position 166 and serine with proline at position 167 in pAOGDH-M40, alanine with isoleucine at position 166 and serine with proline at position 167 in pAOGDH-M41, alanine with lysine at position 166 and serine with proline at position 167 in pAOGDH-M42, alanine with leucine at position 166 and serine with proline at position 167 in pAOGDH-M43, alanine with methionine at position 166 and serine with proline at position 167 in pAOGDH-M44, alanine with proline at position 166 and serine with proline at position 167 in pAOGDH-M45, alanine with serine at position 166 and serine with proline at position 167 in pAOGDH-M46, serine with proline at position 167 and asparagine with lysine at position 169 in pAOGDH-M47, serine with proline at position 167 and asparagine with proline at position 169 in pAOGDH-M48, serine with proline at position 167 and asparagine with tyrosine at position 169 in pAOGDH-M49, serine with proline at position 167 and asparagine with tryptophan at position 169 in pAOGDH-M50, serine with proline at position 167 and leucine with cysteine at position 170 in pAOGDH-M51, serine with proline at position 167 and leucine with phenylalanine at position 170 in pAOGDH-M52, serine with proline at position 167 and leucine with isoleucine at position 171 in pAOGDH-M53, serine with proline at position 167 and leucine with lysine at position 171 in pAOGDH-M54, serine with proline at position 167 and leucine with methionine at position 171 in pAOGDH-M55, serine with proline at position 167 and leucine with glutamine at position 171 in pAOGDH-M56, serine with proline at position 167 and leucine with valine at position 171 in pAOGDH-M57, serine with proline at position 167 and valine with alanine at position 172 in pAOGDH-M58, serine with proline at position 167 and valine with cysteine at position 172 in pAOGDH-M59, serine with proline at position 167 and valine with glutamic acid at position 172 in pAOGDH-M60, serine with proline at position 167 and valine with isoleucine at position 172 in pAOGDH-M61, serine with proline at position 167 and valine with methionine at position 172 in pAOGDH-M62, serine with proline at position 167 and valine with cysteine at position 172 in pAOGDH-M63, serine with proline at position 167 and valine with glutamic acid at position 172 in pAOGDH-M64, serine with proline at position 167 and valine with tryptophan at position 172 in pAOGDH-M65, serine with proline at position 167 and valine with tyrosine at position 172 in pAOGDH-M66, serine with proline at position 167 and valine with glutamine at position 329 in pAOGDH-M67, serine with proline at position 167 and alanine with cysteine at position 331 in pAOGDH-M68, serine with proline at position 167 and alanine with aspartic acid at position 331 in pAOGDH-M69, serine with proline at position 167 and alanine with isoleucine at position 331 in pAOGDH-M70, serine with proline at position 167 and alanine with lysine at position 331 in pAOGDH-M71, serine with proline at position 167 and alanine with leucine at position 331 in pAOGDH-M72, serine with proline at position 167 and alanine with methionine at position 331 in AOGDH-M73, serine with proline at position 167 and alanine with valine at position 331 in pAOGDH-M74 are identified. The results are shown in Table 3.

TABLE 3

| Amino Acid Substitutions | Heat Stability (%) |
| --- | --- |
| G160E + S167P | 28.3 |
| G160I + S167P | 46.3 |
| G160S + S167P | 33.9 |
| G160Q + S167P | 31.8 |
| S162A + S167P | 38.9 |
| S162C + S167P | 21.3 |
| S162D + S167P | 31.0 |
| S162E + S167P | 22.2 |
| S162F + S167P | 43.2 |
| S162H + S167P | 21.3 |
| S162L + S167P | 38.9 |
| G163D + S167P | 28.1 |
| S164F + S167P | 27.9 |
| S164T + S167P | 32.0 |
| S164Y + S167P | 28.3 |
| L165A + S167P | 31.8 |
| L165I + S167P | 22.6 |
| L165N + S167P | 24.3 |
| L165P + S167P | 25.8 |
| L165V + S167P | 33.8 |
| A166C + S167P | 32.3 |
| A166I + S167P | 26.0 |
| A166K + S167P | 37.1 |
| A166L + S167P | 21.3 |
| A166M + S167P | 31.6 |
| A166P + S167P | 38.1 |
| A166S + S167P | 22.5 |
| S167P + N169K | 33.0 |
| S167P + N169P | 33.8 |
| S167P + N169Y | 42.3 |
| S167P + N169W | 31.3 |
| S167P + L170C | 20.4 |
| S167P + L170F | 36.6 |
| S167P + S171I | 42.0 |
| S167P + S171K | 46.1 |
| S167P + S171M | 20.9 |
| S167P + S171Q | 30.0 |
| S167P + S171V | 47.8 |
| S167P + V172A | 35.6 |
| S167P + V172C | 38.4 |
| S167P + V172E | 37.0 |
| S167P + V172I | 40.8 |
| S167P + V172M | 30.0 |
| S167P + V172S | 35.9 |
| S167P + V172T | 37.3 |
| S167P + V172W | 42.0 |
| S167P + V172Y | 30.0 |
| S167P + V329Q | 21.8 |
| S167P + A331C | 34.3 |
| S167P + A331D | 36.1 |
| S167P + A331I | 26.4 |
| S167P + A331K | 33.4 |
| S167P + A331L | 31.7 |
| S167P + A331M | 30.9 |
| S167P + A331V | 26.9 |
| G163K + V551C | 85.9 |
| G163R + V551C | 84.9 |
| Wild Type | 17.7 |

Example 6

Obtaining Modified FADGDH Derived from *Aspergillus oryzae*

To produce modified FADGDH, commercially-available *Escherichia coli* competent cells (*E. coli* DH5; product of Toyobo Co., Ltd.) were transformed using FADGDH, pAOGDH-M10, pAOGDH-M15, pAOGDH-M75, and pAOGDH-M76. The transformants obtained were cultured in TB medium at 25° C. for 24 hours using 10 L jar fermenters. The cells cultured were collected by centrifugation and suspended in 50 mM phosphate buffer (pH6.5). After eliminating nucleic acid, the suspension was centrifuged to obtain the supernatant. Saturating amounts of ammonium sulfate were dissolved into the supernatant, and the target protein was precipitated by centrifugation. The precipitate was re-dissolved in 50 mM phosphate buffer (pH6.5). The solution was gel filtrated using a G-25 Sepharose column, and hydrophobic chromatography with an Octyl-Sepharose column and Phenyl-Sepharose column (elution conditions: each peak fraction was extracted under 25% to 0% saturate ammonium sulfate concentration gradients) was performed. Ammonium sulfate was further eliminated from the resulting peak fraction using a G-25 Sepharose column. In such, samples of the modified FADGDH were prepared. Table 4 shows the improved heat stability of the modified FADGDH even in the purified preparation.

TABLE 4

| Positions of Amino Acid Substitutions | Heat Stability (%) |
| --- | --- |
| S167P | 46.0 |
| V551C | 63.9 |
| G163K + V551C | 84.6 |
| G163R + V551C | 85.9 |
| Wild Type | 17.7 |

Example 7 pH Stability

The pH stabilities of the purified samples prepared in Example 6 were examined. Buffer solutions in the range of pH 3.5 to 8.5 (pH 3.5 to 6.3:0.1M acetic acid buffer, pH 6.3 to 7.3:0.1 M PIPES buffer, pH 7.3 to 8.5:0.1M tris-HCl buffer, pH 6.0 to 7.7:0.1M phosphate buffer) were prepared. Using the buffer solutions, each GDH was diluted to an enzyme concentration level of 1 U/ml. The diluents were incubated at 25° C. for 16 hours, and the resulting enzyme activities before and after incubation were compared. FIG. 1 is a graph illustrating the residual activity ratio after incubation over that of before incubation. As shown in FIG. 1, the enzyme is stable in a wider range of pH levels.

Example 8

Introducing Mutation into the FADGDH Gene Derived from *Aspergillus terreus*

The inventors have successfully cloned the GDH gene derived from *Aspergillus oryzae* and obtained the base sequence information. The inventors screened for heat stable GDH and the amino acid positions responsible for heat stability improvement were identified. A putative amino acid sequence of GDH derived from *Aspergillus oryzae* and a putative amino acid sequence of GDH derived from *Aspergillus terreus* were aligned, and the amino acid residues of *Aspergillus terreus* GDH that correspond to the improved stability of GDH derived from *Aspergillus oryzae* were identified.

Mutagenesis was performed using a QuickChange™ Site-Directed Mutagenesis Kit (product of Stratagene) according to the instructions to make modified FADGDH mutant plasmids having the ability to produce glucose dehydrogenase. Plasmid pAtGDH-s2-7 prepared in Experiment 6 was used as a template. For primer sets, a synthetic oligonucleotide designed to have several sorts of amino acids substituting lysine at position 116 and the complementary synthetic oligonucleotide thereof, a synthetic oligonucleotide designed to have several sorts of amino acids substituting glutamine at position 159 and the complementary synthetic oligonucleotide thereof, a synthetic oligonucleotide designed to have several sorts of amino acids substituting glutamic acid at position 161 and the complementary synthetic oligonucleotide thereof, a synthetic oligonucleotide designed to have several sorts of amino acids substituting asparagine at position 164 and the complementary synthetic oligonucleotide thereof, a synthetic oligonucleotide designed to have several sorts of amino acids substituting threonine at position 166 and the complementary synthetic oligonucleotide thereof, a synthetic oligonucleotide designed to have several sorts of amino acids substituting threonine at position 167 and the complementary synthetic oligonucleotide thereof, a synthetic oligonucleotide designed to have several sorts of amino acids substituting glycine at position 175 and the complementary synthetic oligonucleotide thereof, a synthetic oligonucleotide designed to have several sorts of amino acids substituting serine at position 325 and the complementary synthetic oligonucleotide thereof, a synthetic oligonucleotide designed to have several sorts of amino acids substituting serine at position 327 and the complementary synthetic oligonucleotide thereof, a synthetic oligonucleotide designed to have several sorts of amino acids substituting glutamine at position 365 and the complementary synthetic oligonucleotide thereof, a synthetic oligonucleotide designed to have several sorts of amino acids substituting valine at position 547 and the complementary synthetic oligonucleotide thereof were used. After the transformation of commercially-available *Escherichia coli* competent cells (*E. coli* DH5; product of Toyobo Co., Ltd.), the transformants were applied to agar culture medium (1% polypeptone, 0.5% yeast extract, 0.5% NaCl, 1.5% agar; pH7.3) containing ampicillin, and then incubated at 30° C. overnight.

Example 9

Preparation of Crude Enzyme Solutions Containing Modified FADGDH Derived from *Aspergillus terreus*

The obtained colonies were further inoculated into LB liquid medium supplemented with ampicillin (100 μg/ml) and incubated while shaking overnight at 30° C. The cells obtained by centrifugation of a part of the culture solution were recovered and disrupted in 50 mM phosphate buffer solution (pH 7.0) using glass beads to prepare crude enzyme solutions.

Example 10

Screening of Mutants with Improved Heat Stability

The glucose dehydrogenase activities were measured via the activity measuring method described above, using the crude enzyme solutions prepared in Example 9. The crude enzyme solutions were further heated at 50° C. for 15 minutes, and then the glucose dehydrogenase activities were measured.

These FADGDH gene sequences were verified using a DNA sequencer (ABI PRISM™ 3700DNA Analyzer, product of Perkin-Elmer). Table 5 shows the residual activity ratios (%) of the activities after heat treatment over the activities before heat treatment. These results demonstrate that *Aspergillus-terreus*-derived glucose dehydrogenase with improved heat stability can be obtained using a recombinant.

TABLE 5

| Mutant Amino Acids | 50° C. × 15 min Residual Activity Ratio (%) |
|---|---|
| K116D | 38 |
| K116G | 39 |
| K116L | 44 |
| K116F | 63 |
| K116Q | 42 |
| Q159A | 44 |
| Q159K | 76 |
| Q159N | 54 |
| Q159P | 44 |
| Q159V | 44 |
| Q159L | 35 |
| E161C | 52 |
| N164Y | 58 |
| N164V | 83 |
| N164C | 48 |
| T166F | 88 |
| T166Y | 84 |
| T166W | 77 |
| T167L | 50 |
| T167V | 61 |
| T167S | 43 |
| G175K | 43 |
| S325A | 44 |
| S325G | 35 |
| S325K | 45 |
| S325Q | 40 |
| S325R | 38 |
| S325T | 41 |
| S325V | 36 |
| S325Y | 36 |
| S327E | 35 |
| Q365R | 35 |
| V547S | 71 |
| V547C | 44 |
| V547A | 87 |
| V547Q | 73 |
| Before Modification | 28 |

Furthermore, the substrate specificities to various saccharides were measured in terms of the enzyme activity in accordance with the activity measuring method described above. The dehydrogenase activity value for a glucose substrate solution and the dehydrogenase activity value for, in place of the glucose substrate solution, a comparative saccharide (e.g., maltose) substrate solution having a molar concentration equivalent to the glucose substrate solution were measured, and relative value was determined taking the value obtained with the glucose substrate as 100.

Example 11

Mutant Introduction into FADGDH Gene

Commercial *E. coli* competent cells (*E. coli* DH5, product of Toyobo Co., Ltd.) were transformed using a recombinant plasmid pAOGDH-S2 containing the gene (SEQ ID No. 1) coding for wild-type FADGDH. The transformants were inoculated into ampicillin (50 µg/ml, product of Nacalai Tesque, Inc.)-containing liquid culture medium (1% polypeptone, 0.5% yeast extract, 0.5% NaCl; pH 7.3) and incubated while shaking overnight at 30° C. Using the thus obtained cells, plasmids were prepared using a standard method. Mutagenesis was performed using a QuickChange™ Site-Directed Mutagenesis Kit (product of Stratagene) according to the manufacturer's protocol with the synthetic oligonucleotide of SEQ ID No. 49 designed to have several sorts of amino acids substituting glycine at position 53 and the synthetic oligonucleotide complementary thereto, whereby a modified FADGDH mutant plasmid capable of producing glucose dehydrogenase was obtained. The thus obtained plasmid was prepared in the same manner as in the above method.

Example 12

Preparation of Crude Enzyme Solution Containing Modified FADGDH

Commercial *E. coli* competent cells (*E. coli* DH5, product of Toyobo Co., Ltd.) were transformed using plasmid pAOGDH-S2 prepared in Example 2, and the transformants were then applied to ampicillin-containing agar medium (1% polypeptone, 0.5% yeast extract, 0.5% NaCl, 1.5% agar; pH 7.3). The culture medium was incubated while shaking overnight at 30° C., and the colonies obtained were further inoculated into LB liquid medium supplemented with ampicillin (100 µg/ml) and further incubated while shaking overnight at 30° C. The cells obtained by centrifugation from a part of the culture solution were recovered and disrupted using glass beads in 50 mM phosphate buffer solution (pH 7.0) to prepare a crude enzyme solution.

Example 13

Screening of Mutants with Enhanced Substrate Specificities

Using the crude enzyme solution obtained in Example 3, the activities were measured with the glucose substrate and the xylose substrate employing the activity measuring method described above, and 7 had improved substrate specificities. The plasmids coding for these modified mutants were termed pAOGDH-M1, pAOGDH-M2, pAOGDH-M3, pAOGDH-M4, pAOGDH-M5, pAOGDH-M6, and pAOGDH-M7.

To identify the mutation sites of pAOGDH-M1, pAOGDH-M2, pAOGDH-M3, pAOGDH-M4, pAOGDH-M5, pAOGDH-M6, and pAOGDH-M7, the base sequence of the glucose-dehydrogenase-coding genes were determined using a DNA sequencer (ABI PRISM™ 3700DNA Analyzer, product of Perkin-Elmer). The results confirmed the substitutions of glycine with cysteine at position 53 in the sequence represented by SEQ ID No. 2 in pAOGDH-M1, glycine with histidine at position 53 in the sequence represented by SEQ ID No. 2 in pAOGDH-M2, glycine with lysine at position 53 in the sequence represented by SEQ ID No. 2 in pAOGDH-M3, glycine with methionine at position 53 in the sequence represented by SEQ ID No. 2 in pAOGDH-M4, glycine with asparagine at position 53 in the sequence represented by SEQ ID No. 2 in pAOGDH-M5, glycine with threonine at position 53 in the sequence represented by SEQ ID No. 2 in pAOGDH-M6, and glycine with valine at position 53 in the sequence represented by SEQ ID No. 2 in pAOGDH-M6. Table 6 shows the results.

TABLE 6

| Mutation Sites | Substrate Specificities (%) |
|---|---|
| G53C | 4.3 |
| G53H | 2.5 |
| G53K | 2.8 |
| G53M | 3.1 |
| G53N | 2.9 |
| G53T | 4.8 |
| G53V | 4.4 |
| Wild Type | 9.6 |

Example 14

Production of Mutants Having Improved Substrate Specificity and/or Heat Stability Mutagenesis was performed in the same manner as in Example 2 using a synthetic oligonucleotide of SEQ ID No. 50 designed to have proline substituting serine at position 164 and the synthetic oligonucleotide complementary thereto with plasmid pAOGDH-M2 prepared in Example 13 as a template; using a synthetic oligonucleotide of SEQ ID No. 50 designed to have proline substituting serine at position 164 and the synthetic oligonucleotide complementary thereto with plasmid pAOGDH-M5 as a template; using a synthetic oligonucleotide of SEQ ID No. 51 designed to have arginine substituting glycine at position 163 and the synthetic oligonucleotide complementary thereto with plasmid pAOGDH-M2 as a template; and further using a synthetic oligonucleotide of SEQ ID No. 52 designed to have valine substituting with cysteine at position 551 and the synthetic oligonucleotide complementary thereto (template). Modified FADGDHs with outstanding substrate specificity and/or heat stability were thus obtained, and the obtained plasmids were prepared in the same manner as above. To identify mutation sites, base sequences of the glucose-dehydrogenase-coding genes were determined using a DNA sequencer (ABI PRISM™ 3700DNA Analyzer, product of Perkin-Elmer). The results verified the substitutions of glycine with histidine at position 53 and serine with proline at position 167 in the sequence represented by SEQ ID No. 2 in pAOGDH-M8; glycine with asparagine at position 53 and serine with proline at position 167 in the sequence represented by SEQ ID No. 2 in pAOGDH-M9; and glycine with asparagine at position 53, glycine with arginine at position 163 and valine with cysteine at position 551 in the sequence represented by SEQ ID No. 2 in pAOGDH-M10. The activities were measured using glucose substrate and xylose substrate by the same measuring method as described in Example 4, and enhanced substrate specificities were verified in pAOGDH-M8, pAOGDH-M9 and pAOGDH-M10. To measure heat stabilities, crude enzyme solutions of pAOGDH-M8, pAOGDH-M9 and pAOGDH-M10 were prepared in the same manner as in Example 3, and glucose dehydrogenase activities were measured using the above measuring method. Further, the crude enzyme solutions were heated at 50° C. for 15 minutes, and their respective glucose dehydrogenase activities were measured. Improved heat stabilities were verified in pAOGDH-M8, pAOGDH-M9 and pAOGDH-M10. Table 7 shows the results.

TABLE 7

| Mutation Sites | Substrate Specificities (%) | Heat Stabilities (%) |
|---|---|---|
| G53H + S167P | 2.9 | 27.1 |
| G53N + S167P | 2.8 | 30.3 |
| G53N + G163R + V551C | 3.3 | 84.2 |
| Wild Type | 10.0 | 17.2 |

Example 15

Obtainment of Modified FADGDH

Commercial *E. coli* competent cells (*E. coli* DH5, product of Toyobo Co., Ltd.) were transformed using pAOGDH-M8, pAOGDH-M9 and pAOGDH-M10 to use as modified FADGDH-producing cells. Each of the obtained transformants was incubated at 25° C. for 24 hours in a 10-liter jar fermenter loaded with TB medium. The cultured cells were collected using centrifugation, suspended in 50 mM phosphate buffer (pH 6.5), and subjected to nucleic acid removal, whereby the supernatants were obtained using centrifugation. Ammonium sulfate was dissolved therein to saturation so as to precipitate the target proteins. The precipitate collected during centrifugation was re-dissolved in 50 mM phosphate buffer (pH6.5). Subsequently, the solution was subjected to gel filtration using a G-25 spheres column, and hydrophobic chromatography using an Octyl-sepharose column and a Phenyl-sepharose column (elute conditions: each peak fraction was extracted with 25% to 0% saturate ammonium sulfate concentration gradients). Ammonium sulfate was further removed by gel filtration using G-25 sepharose column, thereby obtaining modified FADGDH samples. As shown in Table 8, the heat stability is enhanced even in the purified samples.

TABLE 8

| Mutation Sites | Substrate Specificities (%) | Heat Stabilities (%) |
|---|---|---|
| G53H + S167P | 2.6 | 27.1 |
| G53N + S167P | 2.7 | 30.3 |
| G53N + G163R + V551C | 3.3 | 80.2 |
| Wild Type | 9.6 | 17.8 |

INDUSTRIAL APPLICABILITY

According to the present invention, the amino acid residues involved with heat stability improvement in FADGDH can be identified which is demonstrated to be applicable to FADGDH derived from various genus and species. Further, the stability improvement of FADGDH provided by the present invention can reduce the heat-inactivation of an enzyme that occurs during production of a glucose measuring reagent, a glucose assay kit and a glucose sensor, thereby enabling reduction of the amount of enzyme to be used improvement in measurement accuracy, hence greatly contributing to industries such as those in medical-related fields.

The invention claimed is:

1. A glucose sensor comprising a modified flavin adenine dinucleotide dependent glucose dehydrogenase (FADGDH) having the amino acid sequence of SEQ ID NO: 2, except that (a) the glycine at position 163 of SEQ ID NO: 2 is substituted with arginine or lysine and (b) the valine at position 551 of SEQ ID NO: 2 is substituted with cysteine.

2. A method for measuring glucose comprising using the glucose sensor of claim 1 to measure glucose of a sample.

* * * * *

SEQUENCE LISTING

<160> NUMBER OF SEQ ID NOS: 52

<210> SEQ ID NO 1
<211> LENGTH: 1719
<212> TYPE: DNA
<213> ORGANISM: Aspergillus oryzae

<400> SEQUENCE: 1

```
atgaagaaca ctacgacata cgactacatc gttgtgggag gcggcacaag tggtcttgtg      60
gtcgcaaatc gcctttctga gaaccccgat gtctccgttc ttctgcttga ggccggtgct     120
tctgtgttca acaacccgga cgtaaccaac gctaacggtt atggattggc ctttggctcg     180
gccatcgact ggcagtacca gtctattaac caaagctatg caggaggtaa acagcaagtt     240
ctgcgtgctg gtaaggccct tggaggaacc agtacaatca atggaatggc ctataccgc      300 gcagaggatg tccagattga cgtttggcag aaacttggaa acgaaggttg gacgtggaaa     360
gatctcctac catactacct gaagagtgaa aacttgacgg cccctaccag ctctcaggtt     420
gctgctggcg ctgcttataa ccctgccgtg aatggaaaag aaggtcctct caaggtcggc     480
tggtcgggaa gcctggcctc cggtaatctg tcagttgctc tgaaccgtac gttccaagcc     540
gctggtgttc catgggttga ggatgtcaat ggaggcaaga tgcgtggctt caacatctac     600
ccatccaccc tcgacgttga cctcaatgtc cgcgaagatc agcccgggc atactacttc     660 ccttatgatg acaggaagaa ccttcacctg ctggagaaca ccactgccaa ccgccttttc     720
```

-continued

```
tggaagaacg gctctgctga ggaagctatt gcggatggtg tcgagatcac ctccgctgat      780
ggcaaggtca ctcgtgtgca tgcaaagaaa gaggtcatca tctctgctgg tgccctgcgg      840
tctcctctca ttctcgagct ttcaggagtt ggaaacccaa ccatcctcaa aaagaacaac      900
ataaccccac gtgtcgatct ccccaccgtt ggggagaacc tccaagacca gttcaacaac      960
ggcatggctg cgaaggata cggcgtcctt gccggtgcct caaccgtgac ctacccttcc      1020
atctccgacg tcttcggtaa cgagactgac tctatcgttg catctctccg atctcaactc      1080
tccgactacg ccgccgcgac cgtcaaggtc agcaacggcc acatgaagca ggaggacctt      1140
gagcgcctct accagctcca atttgacctc atcgtcaagg acaaggtccc tatcgccgag      1200
atcctcttcc accccggtgg tggaaacgcc gtgtcctccg aattctgggg cttgcttccc      1260
ttcgcccgtg gcaacatcca cattagctcc aatgacccga ctgctcccgc cgccatcaac      1320
cctaactact ttatgttcga atgggacggc aagagccagg ccggtatcgc caagtacatc      1380
aggaagattc tccgcagcgc accattgaac aaacttattg cgaaggaaac caagcccggt      1440
ctctctgaga ttccggccac tgctgcggat gagaagtggg ttgaatggct caaggctaac      1500
tatcgttcca acttccaccc cgtcggaact gctgccatga tgcctcgttc cattggtggc      1560
gttgttgata accgtctccg ggtctatggt accagcaatg ttcgcgtcgt agatgcgtct      1620
gtcctgccct ccaggtttg cggccacttg gttagcacgc tttatgccgt tgccgagcgc      1680
gcttccgact tgattaagga ggatgcgaag agtgcttag                             1719
```

<210> SEQ ID NO 2
<211> LENGTH: 572
<212> TYPE: PRT
<213> ORGANISM: Aspergillus oryzae

<400> SEQUENCE: 2

```
Met Lys Asn Thr Thr Tyr Asp Tyr Ile Val Val Gly Gly Gly Thr
1               5                   10                  15

Ser Gly Leu Val Val Ala Asn Arg Leu Ser Glu Asn Pro Asp Val Ser
            20                  25                  30

Val Leu Leu Leu Glu Ala Gly Ala Ser Val Phe Asn Asn Pro Asp Val
        35                  40                  45

Thr Asn Ala Asn Gly Tyr Gly Leu Ala Phe Gly Ser Ala Ile Asp Trp
    50                  55                  60

Gln Tyr Gln Ser Ile Asn Gln Ser Tyr Ala Gly Gly Lys Gln Gln Val
65                  70                  75                  80

Leu Arg Ala Gly Lys Ala Leu Gly Gly Thr Ser Thr Ile Asn Gly Met
                85                  90                  95

Ala Tyr Thr Arg Ala Glu Asp Val Gln Ile Asp Val Trp Gln Lys Leu
            100                 105                 110

Gly Asn Glu Gly Trp Thr Trp Lys Asp Leu Leu Pro Tyr Tyr Leu Lys
        115                 120                 125

Ser Glu Asn Leu Thr Ala Pro Thr Ser Ser Gln Val Ala Ala Gly Ala
    130                 135                 140

Ala Tyr Asn Pro Ala Val Asn Gly Lys Glu Gly Pro Leu Lys Val Gly
145                 150                 155                 160

Trp Ser Gly Ser Leu Ala Ser Gly Asn Leu Ser Val Ala Leu Asn Arg
                165                 170                 175

Thr Phe Gln Ala Ala Gly Val Pro Trp Val Glu Asp Val Asn Gly Gly
            180                 185                 190

Lys Met Arg Gly Phe Asn Ile Tyr Pro Ser Thr Leu Asp Val Asp Leu
        195                 200                 205
```

Asn Val Arg Glu Asp Ala Ala Arg Ala Tyr Tyr Phe Pro Tyr Asp Asp
    210                 215                 220

Arg Lys Asn Leu His Leu Leu Glu Asn Thr Thr Ala Asn Arg Leu Phe
225                 230                 235                 240

Trp Lys Asn Gly Ser Ala Glu Ala Ile Ala Asp Gly Val Glu Ile
                245                 250                 255

Thr Ser Ala Asp Gly Lys Val Thr Arg Val His Ala Lys Lys Glu Val
            260                 265                 270

Ile Ile Ser Ala Gly Ala Leu Arg Ser Pro Leu Ile Leu Glu Leu Ser
        275                 280                 285

Gly Val Gly Asn Pro Thr Ile Leu Lys Lys Asn Asn Ile Thr Pro Arg
    290                 295                 300

Val Asp Leu Pro Thr Val Gly Glu Asn Leu Gln Asp Gln Phe Asn Asn
305                 310                 315                 320

Gly Met Ala Gly Glu Gly Tyr Gly Val Leu Ala Gly Ala Ser Thr Val
                325                 330                 335

Thr Tyr Pro Ser Ile Ser Asp Val Phe Gly Asn Glu Thr Asp Ser Ile
            340                 345                 350

Val Ala Ser Leu Arg Ser Gln Leu Ser Asp Tyr Ala Ala Ala Thr Val
        355                 360                 365

Lys Val Ser Asn Gly His Met Lys Gln Glu Asp Leu Glu Arg Leu Tyr
    370                 375                 380

Gln Leu Gln Phe Asp Leu Ile Val Lys Asp Lys Val Pro Ile Ala Glu
385                 390                 395                 400

Ile Leu Phe His Pro Gly Gly Asn Ala Val Ser Ser Glu Phe Trp
                405                 410                 415

Gly Leu Leu Pro Phe Ala Arg Gly Asn Ile His Ile Ser Ser Asn Asp
            420                 425                 430

Pro Thr Ala Pro Ala Ala Ile Asn Pro Asn Tyr Phe Met Phe Glu Trp
        435                 440                 445

Asp Gly Lys Ser Gln Ala Gly Ile Ala Lys Tyr Ile Arg Lys Ile Leu
    450                 455                 460

Arg Ser Ala Pro Leu Asn Lys Leu Ile Ala Lys Glu Thr Lys Pro Gly
465                 470                 475                 480

Leu Ser Glu Ile Pro Ala Thr Ala Ala Asp Glu Lys Trp Val Glu Trp
                485                 490                 495

Leu Lys Ala Asn Tyr Arg Ser Asn Phe His Pro Val Gly Thr Ala Ala
            500                 505                 510

Met Met Pro Arg Ser Ile Gly Gly Val Val Asp Asn Arg Leu Arg Val
        515                 520                 525

Tyr Gly Thr Ser Asn Val Arg Val Val Asp Ala Ser Val Leu Pro Phe
    530                 535                 540

Gln Val Cys Gly His Leu Val Ser Thr Leu Tyr Ala Val Ala Glu Arg
545                 550                 555                 560

Ala Ser Asp Leu Ile Lys Glu Asp Ala Lys Ser Ala
                565                 570

<210> SEQ ID NO 3
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)

<223> OTHER INFORMATION: "n" may be any nucleotide

<400> SEQUENCE: 3
gaaggtcctc tcaaggtcnn stggtcggga agcctggcc                                      39

<210> SEQ ID NO 4
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 4
ggtcctctca aggtcggcnn stcgggaagc ctggcctcc                                      39

<210> SEQ ID NO 5
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 5
cctctcaagg tcggctggnn sggaagcctg gcctccggt                                      39

<210> SEQ ID NO 6
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 6
ctcaaggtcg gcttgtcgnn sagcctggcc tccctaat                                       39

<210> SEQ ID NO 7
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 7
aaggtcggct ggtcgggann sctggcctcc ggtaatctg                                      39

<210> SEQ ID NO 8
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)

<223> OTHER INFORMATION: "n" may be any nucleotide

<400> SEQUENCE: 8
gtcggctggt cgggaagcnn sgcctccggt aatctgtca        39

<210> SEQ ID NO 9
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 9
ggctggtcgg gaagcctgnn stccggtaat ctgtcagtt        39

<210> SEQ ID NO 10
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (16)..(17)
<223> OTHER INFORMATION: "n" may be any nucleotide

<400> SEQUENCE: 10
tggtcgggaa gcctgnnstc cggtaatctg tcagttgct        39

<210> SEQ ID NO 11
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 11
tcgggaagcc tggcctccnn saatctgtca gttgctctg        39

<210> SEQ ID NO 12
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 12
ggaagcctgg cctccggtnn stcagttgct ctgaaccgt        39

<210> SEQ ID NO 13
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)

<223> OTHER INFORMATION: "n" may be any nucleotide

<400> SEQUENCE: 13
agcctggcct ccggtaatnn stcagttgct ctgaaccgt                                    39

<210> SEQ ID NO 14
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 14
ctggcctccg gtaatctgnn sgttgctctg aaccgtacg                                    39

<210> SEQ ID NO 15
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 15
gcctccggta atctgtcann sgctctgaac cgtacgttct                                   40

<210> SEQ ID NO 16
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 16
gctggcgaag gatacggcnn scttgccggt gcctcaacc                                    39

<210> SEQ ID NO 17
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 17
ggcgaaggat acggcgtcnn sgccggtgcc tcaaccgtg                                    39

<210> SEQ ID NO 18
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)

<223> OTHER INFORMATION: "n" may be any nucleotide

<400> SEQUENCE: 18
gaaggatacg gcgtccttnn sggtgcctca accgtgacc                                39

<210> SEQ ID NO 19
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 19
caggtttgcg gccacttcnn sagcacgctt tatgccgtt                                39

<210> SEQ ID NO 20
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 20
gaaggtcctc tcaaggtcnn stcgggaagc ctggccccg                                39

<210> SEQ ID NO 21
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 21
ggtcctctca aggtcggcnn sggaagcctg gccccgggt                                39

<210> SEQ ID NO 22
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 22
cctctcaagg tcggctggnn sggaagcctg gccccgggt                                39

<210> SEQ ID NO 23
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)

<223> OTHER INFORMATION: "n" may be any nucleotide

<400> SEQUENCE: 23
ctcaaggtcg gcttgtcgnn sagcctggcc ccgggtaat             39

<210> SEQ ID NO 24
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 24
ctcaaggtcg gctggtcgnn sagcctggcc ccgggtaat             39

<210> SEQ ID NO 25
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 25
gtcggctggt cgggaagcnn sgccccgggt aatctgtca             39

<210> SEQ ID NO 26
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 26
ggctggtcgg gaagcctgnn sccgggtaat ctgtcagtt             39

<210> SEQ ID NO 27
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 27
tcgggaagcc tggccctgnn saatctgtca gttgctctg             39

<210> SEQ ID NO 28
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)

<223> OTHER INFORMATION: "n" may be any nucleotide

<400> SEQUENCE: 28
ggaagcctgg ccccgggtnn sctgtcagtt gctctgaac                          39

<210> SEQ ID NO 29
<211> LENGTH: 38
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (18)..(19)
<223> OTHER INFORMATION: "n" may be any nucleotide

<400> SEQUENCE: 29
agcctggccc cggtaatnns tcagttgctc tgaaccgt                           38

<210> SEQ ID NO 30
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 30
ctggccccgg gtaatctgnn sgttgctctg aaccgtacg                          39

<210> SEQ ID NO 31
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 31
gccccgggta atctgtcann sgctctgaac cgtacgttc                          39

<210> SEQ ID NO 32
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 32
gctggcgaag gatacggcnn scttgccggt gcctcaacc                          39

<210> SEQ ID NO 33
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)

<223> OTHER INFORMATION: "n" may be any nucleotide

<400> SEQUENCE: 33
ggcgaaggat acggcgtcnn sgccggtgcc tcaaccgtg                                      39

<210> SEQ ID NO 34
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 34
gaaggatacg gcgtccttnn sggtgcctca accgtgacc                                      39

<210> SEQ ID NO 35
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 35
caggtttgcg gccacttcnn sagcacgctt tatgccgtt                                      39

<210> SEQ ID NO 36
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n" may be any nucleotide

<400> SEQUENCE: 36
ctcaaggtcg gctggtcgnn sagcctggcc tccggtaat                                      39

<210> SEQ ID NO 37
<211> LENGTH: 14
<212> TYPE: PRT
<213> ORGANISM: Artificial
<220> FEATURE:
<223> OTHER INFORMATION: Synthetic

<400> SEQUENCE: 37

Ile Gly Gly Val Val Asp Thr Ser Leu Lys Val Tyr Gly Thr
1               5                   10

<210> SEQ ID NO 38
<211> LENGTH: 20
<212> TYPE: PRT
<213> ORGANISM: Artificial
<220> FEATURE:
<223> OTHER INFORMATION: Synthetic

<400> SEQUENCE: 38

Trp Gly Gly Gly Thr Lys Gln Thr Val Arg Ala Gly Lys Ala Leu Gly
1               5                   10                  15

Gly Thr Ser Thr
            20

<210> SEQ ID NO 39
<211> LENGTH: 34
<212> TYPE: DNA
<213> ORGANISM: Artificial
<220> FEATURE:
<223> OTHER INFORMATION: Synthetic

<400> SEQUENCE: 39
ggaattccat atgctcttct cactggcatt cctg                              34

<210> SEQ ID NO 40
<211> LENGTH: 35
<212> TYPE: DNA
<213> ORGANISM: Artificial
<220> FEATURE:
<223> OTHER INFORMATION: Synthetic

<400> SEQUENCE: 40
cgggatccga attggtacgg gacactgtcc ctacg                             35

<210> SEQ ID NO 41
<211> LENGTH: 1779
<212> TYPE: DNA
<213> ORGANISM: Aspergillus oryzae

<400> SEQUENCE: 41
atgctcttct cactggcatt cctgagtgcc ctgtcgctgg ccacggcatc accggctgga      60
cgggccaaga acactacgac atacgactac atcgttgtgg gaggcggcac aagtggtctt     120
gtggtcgcaa atgccttttc tgagaacccc gatgtctccg ttcttctgct tgaggccggt     180
gcttctgtgt tcaacaaccc ggacgtaacc aacgctaacg gttatggatt ggcctttggc     240
tcggccatcg actggcagta ccagtctatt aaccaaagct atgcaggagg taaacagcaa     300
gttctgcgtg ctggtaaggc ccttggagga accagtacaa tcaatggaat ggcctatacc     360
cgcgcagagg atgtccagat tgacgtttgg cagaaacttg gaaacgaagg ttggacgtgg     420
aaagatctcc taccatacta cctgaagagt gaaaacttga cggcccctac cagctctcag     480
gttgctgctg cgctgctta taaccctgcc gtgaatggaa agaaggtcc tctcaaggtc     540
ggctggtcgg aagcctggc tccggtaat ctgtcagttg ctctgaaccg tacgttccaa     600
gccgctggtg ttccatgggt tgaggatgtc aatggaggca agatgcgtgg cttcaacatc     660
tacccatcca ccctcgacgt tgacctcaat gtccgcgaag atgcagcccg gcatactac      720
ttcccttatg atgacaggaa gaaccttcac ctgctggaga acaccactgc caaccgcctt     780
ttctggaaga acggctctgc tgaggaagct attgcggatg tgtcgagat cacctccgct     840
gatggcaagg tcactcgtgt gcatgcaaag aaagaggtca tcatctctgc tggtgccctg     900
cggtctcctc tcattctcga gctttcagga gttggaaacc caaccatcct caaaaagaac     960
aacataaccc cacgtgtcga tctccccacc gttggggaga acctccaaga ccagttcaac    1020
aacggcatgg ctggcgaagg atacggcgtc cttgccggtg cctcaaccgt gacctaccct    1080
tccatctccg acgtcttcgg taacgagact gactctatcg ttgcatctct ccgatctcaa    1140
ctctccgact acgccgccgc gaccgtcaag gtcagcaacg ccacatgaa gcaggaggac    1200
cttgagcgcc tctaccagct ccaatttgac ctcatcgtca aggacaaggt ccctatcgcc    1260
gagatcctct tccaccccgg tggtggaaac gccgtgtcct ccgaattctg gggcttgctt    1320
cccttcgccc gtggcaacat ccacattagc tccaatgacc cgactgctcc cgccgccatc    1380

```
aaccctaact actttatgtt cgaatgggac ggcaagagcc aggccggtat cgccaagtac  1440
atcaggaaga ttctccgcag cgcaccattg aacaaactta ttgcgaagga aaccaagccc  1500
ggtctctctg agattccggc cactgctgcg gatgagaagt gggttgaatg gctcaaggct  1560
aactatcgtt ccaacttcca ccccgtcgga actgctgcca tgatgcctcg ttccattggt  1620
ggcgttgttg ataaccgtct ccgggtctat ggtaccagca atgttcgcgt cgtagatgcg  1680
tctgtcctgc ccttccaggt ttgcggccac ttggttagca cgctttatgc cgttgccgag  1740
cgcgcttccg acttgattaa ggaggatgcg aagagtgct               1779
```

<210> SEQ ID NO 42
<211> LENGTH: 593
<212> TYPE: PRT
<213> ORGANISM: Aspergillus oryzae

<400> SEQUENCE: 42

```
Met Leu Phe Ser Leu Ala Phe Leu Ser Ala Leu Ser Leu Ala Thr Ala
1               5                   10                  15

Ser Pro Ala Gly Arg Ala Lys Asn Thr Thr Thr Tyr Asp Tyr Ile Val
                20                  25                  30

Val Gly Gly Gly Thr Ser Gly Leu Val Val Ala Asn Arg Leu Ser Glu
            35                  40                  45

Asn Pro Asp Val Ser Val Leu Leu Glu Ala Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
                100                 105                 110

Thr Ile Asn Gly Met Ala Tyr Thr Arg Ala Glu Asp Val Gln Ile Asp
            115                 120                 125

Val Trp Gln Lys Leu Gly Asn Glu Gly Trp Thr Trp Lys Asp Leu Leu
        130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
    210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285

Ala Lys Lys Glu Val Ile Ile Ser Ala Gly Ala Leu Arg Ser Pro Leu
    290                 295                 300
```

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
            325                 330                 335

Asp Gln Phe Asn Asn Gly Met Ala Gly Glu Gly Tyr Gly Val Leu Ala
        340                 345                 350

Gly Ala Ser Thr Val Thr Tyr Pro Ser Ile Ser Asp Val Phe Gly Asn
    355                 360                 365

Glu Thr Asp Ser Ile Val Ala Ser Leu Arg Ser Gln Leu Ser Asp Tyr
370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
            405                 410                 415

Val Pro Ile Ala Glu Ile Leu Phe His Pro Gly Gly Asn Ala Val
        420                 425                 430

Ser Ser Glu Phe Trp Gly Leu Leu Pro Phe Ala Arg Gly Asn Ile His
    435                 440                 445

Ile Ser Ser Asn Asp Pro Thr Ala Pro Ala Ala Ile Asn Pro Asn Tyr
450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
            485                 490                 495

Glu Thr Lys Pro Gly Leu Ser Glu Ile Pro Ala Thr Ala Ala Asp Glu
        500                 505                 510

Lys Trp Val Glu Trp Leu Lys Ala Asn Tyr Arg Ser Asn Phe His Pro
    515                 520                 525

Val Gly Thr Ala Ala Met Met Pro Arg Ser Ile Gly Gly Val Val Asp
530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
            565                 570                 575

Ala Val Ala Glu Arg Ala Ser Asp Leu Ile Lys Glu Asp Ala Lys Ser
        580                 585                 590

Ala

<210> SEQ ID NO 43
<211> LENGTH: 37
<212> TYPE: DNA
<213> ORGANISM: Artificial
<220> FEATURE:
<223> OTHER INFORMATION: Synthetic

<400> SEQUENCE: 43
ggaattccat atgaagaaca ctacgacata cgactac                               37

<210> SEQ ID NO 44
<211> LENGTH: 35
<212> TYPE: DNA
<213> ORGANISM: Artificial
<220> FEATURE:
<223> OTHER INFORMATION: Synthetic

<400> SEQUENCE: 44
cgggatccga attggtacgg gacactgtcc ctacg                                 35

```
<210> SEQ ID NO 45
<211> LENGTH: 1776
<212> TYPE: DNA
<213> ORGANISM: Aspergillus terreus

<400> SEQUENCE: 45
atgttgggaa agctctcctt cctcagtgcc ctgtccctgg cagtggcagc acctttgtcc      60
aactccacgt ccgccaaata tgattatatc gttattggag cggtaccag cggtttggcc     120 gtcgcaaacc gtctatcgga ggacccaagc gtgaacgtac tcattctgga ggccggtggc     180
tcggtctgga caatcccaa tgtcacaaac gtgaatggct atgggcttgc atttgggtct     240
gacattgact ggcaatacca gtccgtcaac cagccatatg gaggcaacgt cagtcaagtg     300
ctgcgtgccg gcaaggccct tgtggtact agtactatta cggtatggc ctataccccgc     360 gccgaggatg tccagatcga cgcctgggaa accattggca cacaggatg gacgtggaag     420 aatctgttcc cttactatcg gaagagcgag aacttcactg tccctaccaa atcgcagact     480
tctcttggag cgtcgtatga agctggagcc cacggccacg agggtcccct tgacgttgcc     540
ttcactcaga tcgagtcgaa caacctgacc acctacctca accgtacctt ccagggcatg     600
ggactcccat ggactgagga cgtcaatggc ggaaagatgc gcggctttaa cctatacccc     660
tccaccgtga atcttgagga gtatgttcgc gaagacgccg ctcgtgcata ctactggcct     720
tacaagtccc gtcccaacct gcatgtcctg ctcaacactt tgccaaccg gattgtgtgg     780 gacggcgaag cccgtgatgg cgacatcact gccagtggtg tcgagatcac ttccaggaac     840
ggcactgttc gtgttatcaa tgcggagaag gaagtcattg tctctgccgg cgccttgaag     900
tccccggcta tccttgaact ttccggaatt ggcaaccct a gcgttcttga caagtacaac     960
atccccgtca aggtcaacct ccctactgta ggtgagaacc ttcaggacca ggtgaacagc    1020
cacatggatg cgtcgggcaa cacttccatc tctggaacca aggcagtctc ttaccccgat    1080
gtctatgacg tcttcggtga cgaagccgag tcggtcgcca acagatccg tgccagcctg    1140 aagcaatacg ccgccgacac cgcccaggcc aacggaaaca tcatgaaggc cgccgatctg    1200
gagcgtctct cgaggtccca gtatgacctt attttcaagg gcagagtccc aattgcagaa    1260
gtcctcaact atcctggcag cgcgacgtcc gtgtttgcag aattctgggc cctccttccc    1320
ttcgctcggg gaagtgttca catcggttct tcaaacccgg tcgagtttcc tgtcatcaac    1380
cccaactatt tcatgctcga ctgggacgcg aagagctacg tcgccgttgc aaagtatatc    1440
cgccgctcgt tcgagagcta ccctctcagc agcatcgtta aggagtctac ccctggctat    1500
gatgttatcc cccggaacgc ttctgaacag agctggaaag aatgggtctt tgataagaac    1560
tatcgttcta acttccatcc cgtcggcacg gctgccatga tgcctcgtga aattggcggt    1620
gtcgtggacg agcgtctgaa tgtctatggt actacgaacg tcagagttgt cgatgcctcg    1680
gtgcttccgt tccaggtctg cggtcatttg gtgagcaccc tatacgctgt ggccgaacgg    1740
gcagcggatc tcatcaaggc cgatgctggt cgtcgt                             1776

<210> SEQ ID NO 46
<211> LENGTH: 568
<212> TYPE: PRT
<213> ORGANISM: Aspergillus terreus

<400> SEQUENCE: 46

Met Lys Tyr Asp Tyr Ile Val Ile Gly Gly Gly Thr Ser Gly Leu Ala
1               5                   10                  15

Val Ala Asn Arg Leu Ser Glu Asp Pro Ser Val Asn Val Leu Ile Leu
```

```
                    20                  25                  30
Glu Ala Gly Gly Ser Val Trp Asn Asn Pro Asn Val Thr Asn Val Asn
            35                  40                  45
Gly Tyr Gly Leu Ala Phe Gly Ser Asp Ile Asp Trp Gln Tyr Gln Ser
        50                  55                  60
Val Asn Gln Pro Tyr Gly Gly Asn Val Ser Gln Val Leu Arg Ala Gly
 65                  70                  75                  80
Lys Ala Leu Gly Gly Thr Ser Thr Ile Asn Gly Met Ala Tyr Thr Arg
                85                  90                  95
Ala Glu Asp Val Gln Ile Asp Ala Trp Glu Thr Ile Gly Asn Thr Gly
            100                 105                 110
Trp Thr Trp Lys Asn Leu Phe Pro Tyr Tyr Arg Lys Ser Glu Asn Phe
            115                 120                 125
Thr Val Pro Thr Lys Ser Gln Thr Ser Leu Gly Ala Ser Tyr Glu Ala
        130                 135                 140
Gly Ala His Gly His Glu Gly Pro Leu Asp Val Ala Phe Thr Gln Ile
145                 150                 155                 160
Glu Ser Asn Asn Leu Thr Thr Tyr Leu Asn Arg Thr Phe Gln Gly Met
                165                 170                 175
Gly Leu Pro Trp Thr Glu Asp Val Asn Gly Gly Lys Met Arg Gly Phe
            180                 185                 190
Asn Leu Tyr Pro Ser Thr Val Asn Leu Glu Glu Tyr Val Arg Glu Asp
            195                 200                 205
Ala Ala Arg Ala Tyr Tyr Trp Pro Tyr Lys Ser Arg Pro Asn Leu His
        210                 215                 220
Val Leu Leu Asn Thr Phe Ala Asn Arg Ile Val Trp Asp Gly Glu Ala
225                 230                 235                 240
Arg Asp Gly Asp Ile Thr Ala Ser Gly Val Glu Ile Thr Ser Arg Asn
                245                 250                 255
Gly Thr Val Arg Val Ile Asn Ala Glu Lys Glu Val Ile Val Ser Ala
            260                 265                 270
Gly Ala Leu Lys Ser Pro Ala Ile Leu Glu Leu Ser Gly Ile Gly Asn
            275                 280                 285
Pro Ser Val Leu Asp Lys Tyr Asn Ile Pro Val Lys Val Asn Leu Pro
        290                 295                 300
Thr Val Gly Glu Asn Leu Gln Asp Gln Val Asn Ser His Met Asp Ala
305                 310                 315                 320
Ser Gly Asn Thr Ser Ile Ser Gly Thr Lys Ala Val Ser Tyr Pro Asp
                325                 330                 335
Val Tyr Asp Val Phe Gly Asp Glu Ala Glu Ser Val Ala Lys Gln Ile
            340                 345                 350
Arg Ala Ser Leu Lys Gln Tyr Ala Ala Asp Thr Ala Gln Ala Asn Gly
        355                 360                 365
Asn Ile Met Lys Ala Ala Asp Leu Glu Arg Leu Phe Glu Val Gln Tyr
        370                 375                 380
Asp Leu Ile Phe Lys Gly Arg Val Pro Ile Ala Glu Val Leu Asn Tyr
385                 390                 395                 400
Pro Gly Ser Ala Thr Ser Val Phe Ala Glu Phe Trp Ala Leu Leu Pro
                405                 410                 415
Phe Ala Arg Gly Ser Val His Ile Gly Ser Ser Asn Pro Val Glu Phe
            420                 425                 430
Pro Val Ile Asn Pro Asn Tyr Phe Met Leu Asp Trp Asp Ala Lys Ser
            435                 440                 445
```

```
Tyr Val Ala Val Ala Lys Tyr Ile Arg Arg Ser Phe Glu Ser Tyr Pro
        450                 455                 460

Leu Ser Ser Ile Val Lys Glu Ser Thr Pro Gly Tyr Asp Val Ile Pro
465                 470                 475                 480

Arg Asn Ala Ser Glu Gln Ser Trp Lys Glu Trp Val Phe Asp Lys Asn
                485                 490                 495

Tyr Arg Ser Asn Phe His Pro Val Gly Thr Ala Ala Met Met Pro Arg
            500                 505                 510

Glu Ile Gly Gly Val Val Asp Glu Arg Leu Asn Val Tyr Gly Thr Thr
        515                 520                 525

Asn Val Arg Val Val Asp Ala Ser Val Leu Pro Phe Gln Val Cys Gly
    530                 535                 540

His Leu Val Ser Thr Leu Tyr Ala Val Ala Glu Arg Ala Ala Asp Leu
545                 550                 555                 560

Ile Lys Ala Asp Ala Gly Arg Arg
                565
```

<210> SEQ ID NO 47
<211> LENGTH: 36
<212> TYPE: DNA
<213> ORGANISM: Artificial
<220> FEATURE:
<223> OTHER INFORMATION: Synthetic

<400> SEQUENCE: 47
ggaattccat atgaaatatg attatatcgt tattgg                          36

<210> SEQ ID NO 48
<211> LENGTH: 32
<212> TYPE: DNA
<213> ORGANISM: Artificial
<220> FEATURE:
<223> OTHER INFORMATION: Synthetic

<400> SEQUENCE: 48
cgggatccga agcgatgagt ataggtacct tc                              32

<210> SEQ ID NO 49
<211> LENGTH: 32
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (16)..(18)
<223> OTHER INFORMATION: "n" may be any nucleotide

<400> SEQUENCE: 49
gtaaccaccg ctaacnnnta tggattggcc tt                              32

<210> SEQ ID NO 50
<211> LENGTH: 39
<212> TYPE: DNA
<213> ORGANISM: Artificial
<220> FEATURE:
<223> OTHER INFORMATION: Synthetic

<400> SEQUENCE: 50
tggtcgggaa gcctgggccc gggtaatctg tcagttgct                       39

<210> SEQ ID NO 51
<211> LENGTH: 39
<212> TYPE: DNA

```
<213> ORGANISM: Artificial
<220> FEATURE:
<223> OTHER INFORMATION: Synthetic

<400> SEQUENCE: 51
ctcaaggtcg gctggtcgcg cagcctggcc tccggtaat                              39

<210> SEQ ID NO 52
<211> LENGTH: 39
<212> TYPE: DNA
<213> ORGANISM: Artificial
<220> FEATURE:
<223> OTHER INFORMATION: Synthetic

<400> SEQUENCE: 52
caggtttgcg gccacttgtg cagcacgctt tatgccgtt                              39
```